US009795681B2

(12) United States Patent
Abreu

(10) Patent No.: US 9,795,681 B2
(45) Date of Patent: *Oct. 24, 2017

(54) TAMPER RESISTANT DOSAGE FORM COMPRISING AN ADSORBENT AND AN ADVERSE AGENT

(71) Applicant: Purdue Pharma L.P., Stamford, CT (US)

(72) Inventor: Osvaldo Abreu, New Milford, NJ (US)

(73) Assignee: Purdue Pharma L.P., Stamford, CT (US)

( * ) Notice: Subject to any disclaimer, the term of this patent is extended or adjusted under 35 U.S.C. 154(b) by 15 days.

This patent is subject to a terminal disclaimer.

(21) Appl. No.: 14/206,112

(22) Filed: Mar. 12, 2014

(65) Prior Publication Data

US 2014/0256764 A1  Sep. 11, 2014

Related U.S. Application Data

(63) Continuation of application No. 13/623,029, filed on Sep. 19, 2012, now abandoned, which is a continuation of application No. 10/593,506, filed as application No. PCT/US2005/009734 on Mar. 23, 2005, now Pat. No. 8,298,579.

(60) Provisional application No. 60/558,301, filed on Mar. 30, 2004.

(51) Int. Cl.
| | |
|---|---|
| A61K 47/46 | (2006.01) |
| A61K 9/14 | (2006.01) |
| A61K 9/24 | (2006.01) |
| A61K 31/485 | (2006.01) |
| A61K 33/06 | (2006.01) |
| A61K 33/44 | (2006.01) |
| A61K 36/185 | (2006.01) |
| A61K 36/47 | (2006.01) |
| A61K 45/06 | (2006.01) |
| A61K 9/00 | (2006.01) |
| A61K 9/16 | (2006.01) |
| A61K 9/20 | (2006.01) |
| A61K 9/50 | (2006.01) |

(52) U.S. Cl.
CPC .............. *A61K 47/46* (2013.01); *A61K 9/143* (2013.01); *A61K 9/209* (2013.01); *A61K 9/2081* (2013.01); *A61K 9/5073* (2013.01); *A61K 9/5084* (2013.01); *A61K 31/485* (2013.01); *A61K 33/06* (2013.01); *A61K 33/44* (2013.01); *A61K 36/185* (2013.01); *A61K 36/47* (2013.01); *A61K 45/06* (2013.01); *A61K 9/0031* (2013.01); *A61K 9/0034* (2013.01); *A61K 9/1617* (2013.01); *A61K 9/2077* (2013.01); *A61K 9/2086* (2013.01); *A61K 9/5015* (2013.01)

(58) Field of Classification Search
None
See application file for complete search history.

(56) References Cited

U.S. PATENT DOCUMENTS

| | | |
|---|---|---|
| 3,493,657 A | 2/1970 | Lewenstein et al. |
| 3,642,986 A | 2/1972 | Welch et al. |
| 3,773,955 A | 11/1973 | Pachter et al. |
| 3,966,940 A | 6/1976 | Pachter et al. |
| 4,379,038 A | 4/1983 | Kaetsu et al. |
| 4,457,933 A | 7/1984 | Gordon et al. |
| 4,582,835 A | 4/1986 | Lewis et al. |
| 4,594,249 A | 6/1986 | Procter et al. |
| 4,673,565 A | 6/1987 | Di Luccio et al. |
| 4,761,284 A | 8/1988 | Nishimura |
| 4,772,627 A | 9/1988 | Matsui et al. |
| 4,957,681 A | 9/1990 | Klimesch et al. |
| 4,970,075 A | 11/1990 | Oshlack |
| 4,990,341 A | 2/1991 | Goldie et al. |
| 5,073,379 A | 12/1991 | Klimesch et al. |
| 5,266,331 A | 11/1993 | Oshlack et al. |
| 5,324,351 A | 6/1994 | Oshlack et al. |
| 5,334,392 A | 8/1994 | Cuine et al. |
| 5,356,467 A | 10/1994 | Oshlack et al. |
| 5,451,409 A | 9/1995 | Rencher et al. |
| 5,462,747 A | 10/1995 | Radebaugh et al. |

(Continued)

FOREIGN PATENT DOCUMENTS

| | | |
|---|---|---|
| DE | 4325465 | 2/1995 |
| EP | 1 064 935 | 3/2001 |

(Continued)

OTHER PUBLICATIONS

Martindale, 32nd Edition, 1999, pp. 56, 68, 986 and 987.
Rang, et al., "Opioid Antagonists," Pharmacology, 4th Ed., 2000, p. 601.
International Search Report for PCT/US2015/009734 dated May 10, 2006, 3 pgs.
Written Opinion of the International Searching Authority for PCT/US2015/009734 received May 23, 2006, 7 pgs.

(Continued)

*Primary Examiner* — Jake Vu
(74) *Attorney, Agent, or Firm* — Lowenstein Sandler LLP

(57) ABSTRACT

Pharmaceutical compositions and dosage forms comprising an adsorbent, and an adverse agent, such as an opioid antagonist. In one embodiment, at least a portion of the adverse agent is on the surface or within the micropore structure of an adsorbent material. The pharmaceutical compositions and dosage forms comprising the adsorbent and the adverse agent are useful for preventing or discouraging tampering, abuse, misuse or diversion of a dosage form containing an active pharmaceutical agent, such as an opioid. The present invention also relates to methods for treating a patient with such a dosage form, as well as kits containing such a dosage form with instructions for using the dosage form to treat a patient. The present invention further relates to process for preparing such pharmaceutical compositions and dosage forms.

20 Claims, 5 Drawing Sheets

(56) References Cited

U.S. PATENT DOCUMENTS

| | | | |
|---|---|---|---|
| 5,472,712 | A | 12/1995 | Oshlack et al. |
| 5,478,577 | A | 12/1995 | Sackler et al. |
| 5,492,692 | A | 2/1996 | Digenis et al. |
| 5,508,042 | A | 4/1996 | Oshlack et al. |
| 5,549,912 | A | 8/1996 | Oshlack et al. |
| 5,559,158 | A | 9/1996 | Al-Razzak et al. |
| 5,610,193 | A | 3/1997 | Al-Razzak et al. |
| 5,656,295 | A | 8/1997 | Oshlack et al. |
| 5,846,971 | A * | 12/1998 | Sangekar et al. ........ 514/254.07 |
| 5,935,975 | A | 8/1999 | Rose et al. |
| 5,958,452 | A | 9/1999 | Oshlack et al. |
| 5,965,161 | A | 10/1999 | Oshlack et al. |
| 5,968,551 | A | 10/1999 | Oshlack et al. |
| 6,063,405 | A | 5/2000 | Drizen et al. |
| 6,120,802 | A | 9/2000 | Breitenbach et al. |
| 6,143,328 | A | 11/2000 | Heafield et al. |
| 6,228,863 | B1 | 5/2001 | Palermo et al. |
| 6,261,599 | B1 | 7/2001 | Oshlack et al. |
| 6,294,195 | B1 | 9/2001 | Oshlack et al. |
| 6,306,391 | B1 | 10/2001 | Modi et al. |
| 6,335,033 | B2 | 1/2002 | Oshlack et al. |
| 6,353,145 | B1 * | 3/2002 | Church ........................ 602/48 |
| 6,696,088 | B2 | 2/2004 | Oshlack et al. |
| 6,827,932 | B2 | 12/2004 | Crippen et al. |
| 7,914,818 | B2 | 3/2011 | Breder et al. |
| 2002/0119197 | A1 | 8/2002 | Dyar et al. |
| 2003/0004177 | A1 | 1/2003 | Kao et al. |
| 2003/0065002 | A1 | 4/2003 | Caruso et al. |
| 2003/0073717 | A1 | 4/2003 | Broughton et al. |
| 2003/0143269 | A1 * | 7/2003 | Oshlack et al. ............. 424/468 |
| 2003/0229111 | A1 * | 12/2003 | Oshlack et al. ............. 514/282 |
| 2010/0303935 | A1 | 12/2010 | Squires |

FOREIGN PATENT DOCUMENTS

| | | |
|---|---|---|
| JP | 54-154515 | 12/1979 |
| JP | 6-008220 | 1/1994 |
| WO | WO 97/15293 | 5/1997 |
| WO | WO 99/32119 | 7/1999 |
| WO | WO 01/58451 | 8/2001 |
| WO | WO 01/58477 | 8/2001 |
| WO | 02/051389 | 7/2002 |
| WO | 02051389 | 7/2002 |
| WO | WO 03/013433 | 2/2003 |
| WO | WO 03/013479 | 2/2003 |
| WO | WO 03/013525 | 2/2003 |
| WO | WO 03/013538 | 2/2003 |
| WO | WO 2005/055981 | 6/2005 |
| WO | 2005097075 | 10/2005 |

OTHER PUBLICATIONS

Baker et al., "Activated Carbon" in *Kirk-Othmer Encycl. Of Chem. Technol.* 4: 1015-1022 ($4^{th}$ ed., 1995).
*United States Pharmacopeia* 26: 404 (2003).
*Perry's Chemical Engineers' Handbook* 16: 1-48 ($6^{th}$ ed., 1984).
Ruthven, DM "Adsorption" *Kirk-Othmer Encyc. Of Chem. Technol.* 4: 493-528 ($4^{th}$ ed., 1995).
Gembicki et al., "Adsorption, Liquid Separation" *Kirk-Othmer Encyc. Of Chem. Technol.* 4: 573-600 ($4^{th}$ ed., 1995).
Lee et al., "Controlled-Release Drug-Delivery Systems" ($20^{th}$ ed., 2000) *Remington's: The Science and Practice of Pharmacy* pp. 903-929.
Rudnic et al., "Oral Dosage Forms" *Remington's: The Science and Practice of Pharmacy* pp. 858-885 ($20^{th}$ ed., 2000).
*Remington's: The Science and Practice of Pharmacy* p. 1238 ($20^{th}$ ed., 2000).
CD Roempp Chemie Lexicon, "Antagonisten," Version 1.0, 1995, (in German with machine translation into English).

* cited by examiner

TAMPER RESISTANT DOSAGE FORM COMPRISING AN ADSORBENT AND AN ADVERSE AGENT

This application is a continuation of U.S. patent application Ser. No. 13/623,029, filed Sep. 19, 2012, which is a continuation of U.S. patent application Ser. No. 10/593,506, filed Sep. 20, 2006, now issued as U.S. Pat. No. 8,298,579, which is a U.S. national stage of International App. No. PCT/US2005/009734, filed Mar. 23, 2005, which claims the benefit of U.S. Provisional Application No. 60/558,301, filed Mar. 30, 2004, the disclosure of the provisional application being expressly incorporated by reference herein its entirety for all purposes.

1. FIELD OF THE INVENTION

The present invention relates to pharmaceutical compositions and dosage forms comprising an adsorbent and an adverse agent, such as an opioid antagonist, which are useful for preventing or discouraging tampering, abuse, misuse or diversion of a dosage form containing an active pharmaceutical agent, such as an opioid. The present invention also relates to methods for treating a patient with such a dosage form, as well as kits containing such a dosage form with instructions for using the dosage form to treat a patient. The present invention further relates to processes for preparing such pharmaceutical compositions and dosage forms.

2. BACKGROUND OF THE INVENTION

Considerable efforts have focused on the treatment or prevention of unintended or illicit use of a poison or a pharmaceutically active agent. For example, one treatment for a patient who ingests an excess of a drug or a poison involves
administration of an adsorbent such as activated charcoal (see *Remington's: The Science and Practice of Pharmacy* 1238 (20th ed. 2000)). The activated charcoal is intended to adsorb a portion of the drug or poison and prevent it from entering the circulatory system.

U.S. Pat. No. 4,594,249 to Proctor et al. discloses a method for alleviating the aftereffects of the consumption of alcoholic beverages by administration of activated charcoal to the alcohol consumer immediately before, during or immediately after alcohol consumption.

U.S. Pat. No. 4,761,284 to Nishimura discloses a pharmaceutical composition comprising spherical particles of activated charcoal purportedly useful for adsorbing exogeneous or endogenous toxins in the gastrointestinal tract of a patient without disintegration of the pharmaceutical composition.

U.S. Patent Application Publication No. 2002/0155103 A1 discloses a composition comprising activated charcoal and limestone allegedly useful for preventing or delaying the onset of aftereffects associated with alcohol consumption.

There have also been attempts in the art to increase the tamper resistance of dosage forms, such as opioid analgesic dosage forms. Prior approaches to developing tamper resistant opioid dosage forms have included combining an opioid agonist with an opioid antagonist. Particular examples of such combinations include compositions including methadone and naloxone (U.S. Pat. No. 3,773,955 to Pachter et al.); methadol or acetyl methadol and naloxone (U.S. Pat. No. 3,966,940 to Pachter et al.); oxycodone and naloxone (U.S. Pat. No. 4,457,933 to Gordon et al); and buprenorphine and naloxone (U.S. Pat. No. 4,582,835 to Lewis et al.).

U.S. Pat. No. 6,228,863 to Palermo et al. discloses an oral dosage form which combines an opioid agonist and an opioid antagonist such that at least two separation steps are required to isolate the agonist.

U.S. Pat. No. 5,610,193 to Al-Razzak et al. discloses a pharmaceutical composition comprising a pharmaceutically acceptable HIV protease inhibitor and solvent adsorbed onto a pharmaceutically acceptable adsorbent. The reference alleges that the composition provides improved oral bioavailability of the active compound that is poorly water soluble.

U.S. Pat. No. 6,696,088 B2 to Oshlack et al., and U.S. Patent Application Publication Nos. 2003/00073717 A1, 2003/0004177 A1 and 2003/0065002 A1 disclose oral dosage forms comprising an opioid agonist in releasable form and an opioid antagonist which is substantially not released when the dosage form is administered intact.

There remains a need in the art for improved tamper resistant dosage forms and improved techniques for their preparation.

3. SUMMARY OF THE INVENTION

The present invention relates to pharmaceutical compositions and dosage forms comprising an adsorbent and an adverse agent. The present invention also relates to methods for making such compositions and dosage forms. The present invention still further relates to methods for treating a patient with such pharmaceutical compositions or dosage forms, as well as kits comprising such pharmaceutical compositions or dosage forms and instructions directing the usage of the composition or dosage form to treat a patient. The dosage forms in accordance with the present invention include but are not limited to, oral dosage forms, including but not limited to, capsules or tablets; rectal suppositories; and vaginal suppositories. In certain embodiments, the dosage forms can comprise a plurality of particles.

In one embodiment, the invention relates to a dosage form comprising an adsorbent and an adverse agent. In another embodiment, the present invention relates to a dosage form comprising an active agent, an adsorbent, and an adverse agent.

In another embodiment, the invention relates to a dosage form comprising a plurality of first particles comprising an active agent; and a plurality of second particles comprising an adsorbent and an adverse agent, wherein at least a majority of the adverse agent is adsorbed on the adsorbent. In one embodiment, the invention relates to an oral dosage form comprising a plurality of first particles comprising an opioid agonist; and a plurality of second particles comprising an adsorbent and an opioid antagonist, wherein the first particles provide a controlled release of the opioid agonist upon oral administration to a patient.

In another embodiment, the invention relates to a dosage form comprising a core comprising an adsorbent and an adverse agent; and a shell comprising an active agent, wherein the shell at least partially covers or surrounds the core.

In one embodiment, at least a portion of the adverse agent is adsorbed onto at least a portion of the adsorbent. In another embodiment, at least a majority, i.e., 50 wt. %, of the adverse agent is adsorbed onto at least a portion of the adsorbent. In a further embodiment, essentially all of the adverse agent is absorbed onto at least a portion of the adsorbent.

The compositions and dosage forms of the present invention can provide controlled release, immediate release or delayed release of the active agent and/or the adverse agent.

The invention also relates to methods for preparing a dosage form comprising an adsorbent and an adverse agent. In one embodiment, the invention relates to a method for preparing a dosage form comprising providing an adsorbent; providing a liquid comprising an adverse agent; contacting the adsorbent with the liquid comprising the adverse agent for sufficient time to allow at least a portion of the adverse agent to adsorb onto the adsorbent; separating the adsorbent from the liquid phase; and, optionally, washing the adsorbent.

In another embodiment, the invention relates to a method for preparing a dosage form comprising providing an adsorbent; providing a liquid comprising an adverse agent; adding the adsorbent to a fluidized bed; fluidizing the adsorbent; spraying the liquid onto the fluidized adsorbent; and, optionally, drying the adsorbent.

The invention also relates to a method of treating a condition, or a symptom thereof, comprising administering a dosage form of the invention comprising an adsorbent and an adverse agent to a patient. In one embodiment of the invention, the patient is treated for pain.

The present invention also relates to methods for reducing abuse, misuse or diversion of a dosage form for treating pain, which methods include administering to a patent in need thereof a dosage form of the invention.

In still another embodiment, the invention relates to a kit for treating a patient, including at least one dosage form of the invention and a set of instructions describing the use of the dosage form to treat the patient. In one embodiment of the invention, the kit is for treating a patient's pain.

The present invention can be understood more fully by reference to the following detailed description and examples, which are intended to exemplify non-limiting embodiments of the invention.

4. BRIEF DESCRIPTION OF THE DRAWINGS

5. DETAILED DESCRIPTION OF THE INVENTION

5.1 Definitions

Figure 1A:
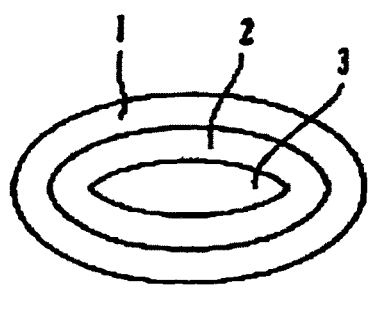
FIGS. 1a, 1b and 1c show perspective views of three embodiments of dosage forms of the invention.

Any reference herein to any pharmaceutical agent, such as an active agent, an adverse agent, an opioid agonist or an opioid antagonist, shall, unless otherwise stated, include any pharmaceutically acceptable form of such pharmaceutical agent, such as the free form, any pharmaceutically acceptable salt form, any pharmaceutically acceptable base form, any pharmaceutically acceptable hydrate, any pharmaceutically acceptable solvate, any stereoisomer, any optical isomer, as well as any prodrug of such pharmaceutical agent and any pharmaceutically active analog of such pharmaceutical agent, and mixtures of any two or more of the foregoing.

The phrase "pharmaceutically acceptable salt," as used herein, can be a salt formed from an acid and the basic group, such as a nitrogen group, of an active agent or an adverse agent. Examples of such salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, -toluenesulfonate, glubionate and palmoate (i.e., 1,1'-methylene-bis-(2-hydroxy-3-naphthoate)) salts. The term "pharmaceutically acceptable salt" can alternatively be a salt prepared from an active agent or an adverse agent having an acidic functional group, such as a carboxylic acid or sulfonic acid functional group, and a pharmaceutically acceptable inorganic or organic base. Examples of such bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methylamine, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

A "patient" or an "animal" is preferably a mammal, and includes, but is not limited to, a cow, monkey, horse, sheep, pig, chicken, turkey, quail, cat, dog, mouse, rat, rabbit and guinea pig, and most preferably a human.

As used herein, the phrase "activated adsorbent" means an adsorbent that has undergone physical and/or chemical processing to increase its adsorptive capacity.

As used herein, the phrase "active agent" refers to a pharmaceutical agent that causes a biological effect when absorbed in sufficient amount into the blood stream of a patient.

As used herein, the phrase "adsorbent" refers to a pharmaceutically acceptable material exhibiting a large surface area and/or micropore volume capable of holding or retaining other molecules or substances onto its surface and/or pores and/or channels.

As used herein, the term "adsorbent/adverse agent" refers to an adsorbent which has adverse agent adsorbed onto at least a portion of its surface and/or pores and/or channels.

As used herein, the phrase "adverse agent" refers to a pharmaceutical agent that partially or completely negates or reverses at least one biological effect of an active agent present in the dosage form, e.g., euphoric effect, or produces one or more unpleasant physiological reactions, e.g., vomiting, nausea, diarrhea, bad taste, when absorbed in sufficient amount into the blood stream of a patient or animal.

As used herein, the term "controlled release" refers to the in vivo release of an active agent from a dosage form in a controlled manner over an extended period of time. For example, a controlled release oral dosage form can release the drug, e.g., over a 5 to 24 h interval.

As used herein, the phrase "delayed release" refers to an in vivo release process in which substantially no active agent is released from a dosage form for at least 1 h following administration. Once the delayed release occurs, the dosage form can release the active agent by a controlled release or by immediate release.

As used herein, the term "laminate" refers to a structure comprising more than one layer, i.e., a multilayer structure.

As used herein, the phrase "opioid agonist" refers to an active agent which binds, optionally stereospecifically, to any one or more of several subspecies of opioid receptors and produces agonist activity.

As used herein, the phrase "opioid antagonist" refers to an adverse agent that either reduces, delays or reverses at least one biological effect of an opioid agonist, e.g., euphoric effect, when absorbed in sufficient amount into the blood stream of a patient or animal.

5.2 Dosage Forms Comprising an Adsorbent and an Adverse Agent

The present invention is directed to pharmaceutical compositions and dosage forms comprising an adsorbent and an adverse agent, and to methods for making such compositions and dosage forms. In certain embodiments, the present invention relates to dosage forms comprising an active agent, an adsorbent and an adverse agent.

In one embodiment, the invention relates to a dosage form comprising a plurality of first particles comprising an active agent; and a plurality of second particles comprising an adsorbent and an adverse agent, wherein at least a majority of the adverse agent is adsorbed on the adsorbent. In another embodiment, the invention relates to an oral dosage form comprising a plurality of first particles comprising an opioid agonist; and a plurality of second particles comprising an adsorbent and an opioid antagonist; wherein at least a majority of the adverse agent is adsorbed on the adsorbent, and wherein the first particles provide a controlled release of the opioid agonist upon oral administration to a patient.

In another embodiment, the invention relates to a dosage form comprising a core comprising an adsorbent and an adverse agent; and a shell comprising an active agent, wherein the shell at least partially covers or surrounds the core.

The compositions and dosage forms of the present invention can provide any rate of release of the active agent, including, but not limited to, controlled release, immediate release or delayed release.

The present invention comprises at least one adsorbent/adverse agent. In certain embodiments, at least a portion of the adverse agent is adsorbed onto at least a portion of the adsorbent. In one embodiment, at least a majority, i.e., at least 50 wt. %, of the adverse agent is adsorbed onto at least a portion of the adsorbent. In other embodiments, the percentage of the adverse agent which is adsorbed onto at least a portion of the adsorbent can be, e.g., at least 70 wt. %, at least 80 wt. %, or at least 90 wt. % or more. In one embodiment, essentially all of the adverse agent is adsorbed onto at least a portion of the adsorbent.

In certain embodiments, the compositions and dosage forms of the invention are formulated or made in a manner which reduces or prevents the in vivo release or absorption of the adverse agent into the blood stream following administration as intended of the intact dosage form to a patient. Thus, in certain embodiments, only a small amount, preferably less than about 10 wt. %, more preferably less than about 1 wt. %, or none, of the adverse agent present in the dosage form is released in vivo or absorbed into the blood stream following the administration as intended of an intact dosage from to a patient. In certain embodiments, when the adverse agent of the adsorbent/adverse agent is an opioid antagonist, preferably less than about 0.5 mg, and more preferably less than about 0.05 mg, of the opioid antagonist is released in vivo following administration as intended of the intact dosage form to a patient.

In certain embodiments, the dosage form of the invention is designed to release a significant amount of the adverse agent in vivo if it is mistreated or misused. For example, an abuser may attempt to crush the dosage form in order to get a powder form of the composition, which form can be expected to provide an immediate release of active agent. In this case, crushing the formulation should expose the adverse agent present in the adverse agent/adsorbent, thereby allowing it to be released if administered. Alternatively, an abuser may attempt to dissolve the formulation in organic solvent, e.g., ethanol, and isolate the active agent from solution. In this case, the extraction step with organic solvent should cause release of a significant portion of the adverse agent, because the adverse agent will desorb or dissolve in the presence of a solvent such as ethanol.

In one embodiment, the adsorbent and adverse agent can be extruded with other materials such as binders, plasticizers, processing aids, excipients, or the like, or combinations of two or more of the foregoing.

In one embodiment, the present invention relates to solid dosage forms including a plurality of particles including an active agent, an adsorbent and an adverse agent, wherein the particles comprise a core comprising the adsorbent and the adverse agent and the core is at least partially surrounded by a shell comprising the active agent. The particles can be made by a process comprising co-extrusion of the core and the shell. Preferably, the shell surrounds a majority of the core component.

In certain embodiments, the adsorbent and the adverse agent can be present throughout the core. In one embodiment, the adsorbent and the adverse agent can be present in both the core and the shell. In another embodiment, the adsorbent and the adverse agent can be present in one or more inner layers of a multilayer particle.

In certain embodiments, the shell does not include any adsorbent/adverse agent. In other embodiments, the shell can include an adsorbent/adverse agent. In one embodiment, the amount of adverse agent present in the shell is less than the amount of adverse agent present in the core. In other embodiments, the shell can comprise an adverse agent that is not an adsorbent/adverse agent, which adverse agent can have any release rate, including but not limited to, immediate release or controlled release.

In one embodiment, the adsorbent and the adverse agent are present only in the core, and the active agent is present only in the shell of a multilayer particle. In this embodiment, it is acceptable for small amounts of active agent and/or adverse agent to migrate to other components or layers following c-extrusion.

In one embodiment, the dosage forms of the invention can comprise one or more particles of any appropriate size. In one embodiment, the dosage form can comprise a plurality of small particles, such as, for example, particles having a size of from about 0.1 mm to about 5.0 mm in all dimensions, preferably from about 0.1 mm to about 3.0 mm in all dimensions. The particles can have any shape, such as cylindrical, spherical, square, ellipsoid, or any regular or irregular form, as desired.

In one embodiment, a dosage form is prepared to include an effective amount of melt-extruded multiparticulates ("MEMs") comprising an active agent within a hard or soft gelatin capsule. For example, a plurality of MEMs containing a core and a shell can be placed in a gelatin capsule in an amount sufficient to provide an effective sustained-release dose of the active agent when ingested and contacted by body fluid, without significant release of the adverse agent from the adsorbent/adverse agent. The particle size of the multiparticulates of the dosage form of the invention is preferably from about 0.1 mm to about 5.0 mm in all dimensions and, more preferably, from about 0.1 mm to about 3.0 mm in all dimensions.

The dosage forms of the invention can be administered orally, such as in the form of a tablet or capsule, or rectally or vaginally, such as in the form of a suppository. In a preferred embodiment, the invention is directed to oral dosage forms.

In certain embodiments, the dosage forms are formulated to provide controlled release of the active agent in vivo, e.g., over about 5 to 8 h, preferably over at least 12 h, more preferably over at least 24 h, or longer.

When an intact dosage form including an active agent and an adsorbent/adverse agent is administered to a patient, only a small amount, and preferably almost none, of the adverse agent is released in vivo, whereas tine active agent is released at the intended rate, which can vary from immediate release to controlled release. However, when a dosage form including an active agent, an adsorbent and an adverse agent is tampered with, e.g., chewed, crushed, ground or dissolved, particularly in a solvent with heat (e.g., greater than from about 45° C. to about 50° C., up to about 100° C. or above), then the amount of adverse agent available for absorption into the body is substantially increased. The adverse agent is then available to exert its effect by either reducing at least one effect of the active agent, e.g., euphoric effect, or eliciting one or more unpleasant effects in the patient. Thus, where the adverse agent is an antagonist of the active agent, at least one effect of the active agent is preferably substantially diminished, or even eliminated, by the effect of the adverse agent. For example, where the active agent is an opioid agonist and the adverse agent is an opioid antagonist, an increased amount of opioid antagonist will become bioavailable when the dosage form is tampered with, interfering with opioid-receptor binding and reducing the opioid agonist's euphoric effect. Accordingly, only patients who take the dosage form of the present invention as intended as an intact dosage form will experience substantially the full pharmacological effect of the active agent. Where the adverse agent is an emetic agent and the dosage form is tampered with, the release and absorption of the emetic agent will induce nausea and/or vomiting to discourage the user from tampering with the dosage form and also, in certain instances, remove the active agent from the subject's body. Abuse of the active agent in the dosage form will thus become less desirable because of the undesirable effects caused by the adverse agent.

It is contemplated by the inventor that the release rate of the active agent and the adverse agent can be measured by in vivo methods or in vitro methods. However, the inventor does not represent that there is necessarily a direct correlation between the results obtained via the two different methods.

When administered as intended to a patient, the in vivo release of any adverse agent from the intact dosage form will preferably be sufficiently low so that it will not substantially reduce the benefits of the active agent or produce any unpleasant physiological reaction. The release rate of the adverse agent will be determined in large part by the composition of the core, the sheath and the shell. The dosage form of the invention will typically release less than about 10 wt. % of, preferably less than about 1 wt. % of, more preferably substantially no adverse agent in vivo following administration as intended of the intact dosage form. When the adverse agent is an opioid antagonist, the dosage form will preferably release less than about 0.5 mg, more preferably less than about 0.05 mg, of the opioid antagonist in vivo following administration as intended of the intact dosage form. For example, in one embodiment, when the adverse agent is naltrexone opioid antagonist, preferably less than 0.0625 mg of naltrexone is released in vivo following administration of the intact dosage form as intended.

In certain embodiments, the dosage form preferably releases less than about 10 wt. %, more preferably less than about 1 wt. %, more preferably substantially no adverse agent over a 36 h period during a standard in vitro dissolution test. For example, when the oral dosage form contains 5.0 mg of opioid antagonist and a dissolution test is conducted using the USP Basket Method (USP Type I basket, 100 rpm; 70O mL simulated gastric filled, pH 1.2 without enzyme; 37° C. for 1 h followed by 900 mL simulated intestinal fluid; pH 7.5 without enzyme for the duration of the test), the quantity of opioid antagonist released in simulated gastrointestinal fluid over 36 h can be less than 0.5 mg, and more preferably less than 0.05 mg.

In one embodiment of the invention, the solid dosage form can optionally be covered by a cosmetic coating. Any known type of cosmetic coating used for pharmaceutical dosage forms can be used so long as the dissolution pattern of the coated dosage form achieves the intended purpose of the invention.

In certain embodiments, the dosage form can be cured by exposure to prolonged elevated temperatures in order to achieve increased stability. As used herein, the term "curing" means the heat treatment of the dosage form (or intermediate product) for purposes of obtaining a stabilized final dosage form. As understood by those skilled in the art, when the formulations of the invention incorporate a polymer as part or all of the hydrophobic retarding agent, a heat treatment causes a curing effect and the polymer possibly cross-links with itself into a more stable state. When the formulations of the invention include a hydrophobic material such as, e.g., hydrogenated vegetable oil or stearyl alcohol, the heat treatment can be more akin to an annealing of the formulation rather than a curing of the polymer. However, for purposes of the present invention, the use of the term "curing" is deemed to encompass both curing and annealing. In situations where the hydrophobic material includes only a wax-like substance, curing can be accomplished at a temperature from about 35° C. to about 65° C., for a time period sufficient to achieve maximum stability, such as for a time period from about 5 to about 72 h. In other embodiments, curing is conducted at a temperature of from about 40° C. to about 60° C., for a time period from about 5 to about 48 h or more, and preferably at least about 24 h. Suitable curing times that achieve the intended result of a stabilized dosage form can be determined by those of skill in the art.

5.3 Adsorbent Materials

Adsorbent materials useful for the present invention are water-insoluble, pharmaceutically acceptable materials that exhibit high surface area when measured by a method such as the Brunauer-Emmett-Teller (BET) model using nitrogen as the adsorptive (see F. S. Baker et al., "Activated Carbon" in *Kirk-Othmer Encyc. of Chem. Technol*, 4:1016 (4th ed. 1995) which is expressly incorporated herein by reference in its entirety for all purposes). Accordingly, in one embodiment, the adsorbent material suitable for use in the present invention exhibits a BET surface area of greater than 100 mg/g. Preferably, the adsorbent material exhibits a BET surface area of greater than 500 mg/g. Most preferably, the adsorbent material exhibits BET surface area of greater than 1000 mg/g.

Non-limiting examples of pharmaceutically acceptable adsorbent materials useful in the invention include one or more of high surface area forms of activated carbon including activated carbon charcoal and activated graphite; activated clays including kaolin, montmorillonite, attapulgite, illite, bentonite and halloysite; activated inorganic metal oxides and/or inorganic ion-exchange resins including silicon dioxide, colloidal silicon dioxide (e.g., CAB-O-SIL, available from Cabot Corp.), and alumina; activated aluminum silicates and/or inorganic ion-exchange compositions such as zeolites; activated organic salts including organic ion-exchange resins such as polystyrene sulfonate; organic polymer-based adsorbents such as, e.g., microcrystalline cellulose, starch, maltodextrin, crospovidone (e.g., POLY-PLAXDONE XL or XL1O, available from GAF Corp.); and the like.

Preferably, the adsorbent material is an activated adsorbent material. Activated adsorbent materials are commercially available and/or are activated by the user immediately prior to use by methods well-known in the art. For example, methods of activating inorganic adsorbents involve removing surface adsorbed species such as, e.g., water, organic compounds and sulfides, using heat in combination with vacuum or an inert purge gas such as nitrogen.

Methods of activating inorganic ion-exchange compositions and organic ion-exchange resins involve treatment with a solution containing a specific salt, allowing an ion of the salt to adsorb onto the surface of the ion-exchange resin material, and, optionally drying the treated resin or material. The activated resin or material is then treated with the salt form of an adverse agent, the adverse agent ion displaces the pre-adsorbed ion, thereby affixing the adverse agent to the ion-exchange resin or material.

In one embodiment, the adsorbent material is selected from the group consisting of activated charcoal, alumina, bentonite and kaolin.

In a preferred embodiment, the adsorbent material is activated charcoal or activated carbon, both terms being used interchangeably herein to refer to a large surface area and/or micropore volume form of carbon containing low level of impurities (see, e.g., *The United States Pharmacopeia* 26404 (Z003)). F. S. Baker et a.l, "Activated Carbon" in *Kirk-Othmer Encyc. of Chem. Technol.*, 4:1015-1022 (4th ed. 1995), which is expressly incorporated herein by reference in its entirety for all purposes, discloses methods for preparing different grades of activated charcoal. Activated charcoal useful in the present invention exhibits a surface area of greater than about 100 m 1 g. In certain embodiments, the surface area of the activated charcoal is from about 300 m/g to about 2,000 $m^2$/g.

The activated adsorbents useful in the present invention also exhibit high adsorptive capacity as measured by their absorbance of the dye methylene blue ("MB value") from aqueous solution (see ASTM D3860-98 (adsorptive capacity of activated carbon) and ASTM C837-99 (adsorptive capacity of clay), each of which is expressly incorporated herein by reference in its entirety for all purposes). In one embodiment, the adsorbent material suitable for use in the preseat invention exhibits a MB value of greater than 30 mg/g; in another embodiment, the adsorbent material exhibits a MB value of greater than 150 mg/g; and in another embodiment, the adsorbent material exhibits a MB value of greater than 300 mg/g.

Non-limiting examples of adsorbent materials useful in the present invention include the activated charcoals listed below in Table 1.

TABLE 1

Exemplary activated charcoal adsorbent materials.

| Sample [a] | Feedstock material | Activation method | Physical form; typical use | Surface area, $m^2$/g | | | Pore volume, $cm^2$ | |
|---|---|---|---|---|---|---|---|---|
| | | | | BET [b] | External (t-plot) | MB [c] value | Micropores (t-plot) | Mesopores (P/P8 = 0.95) |
| Calgon F-300 [d] | Coal | Steam | Pellets; odor and color removal | 901 | 63 | 105 | 0.38 | 0.10 |
| Asbury #5597 [e] | Wood | Steam | Powder; sugar production | 907 | 147 | 183 | 0.36 | 0.22 |
| B&S 207A [f] | Coal | Steam | Pellets; food industry | 977 | 63 | 125 | 0.42 | 0.09 |
| Norit DARCO KBB [g] | Wood | Chemical | Powder; color removal | 1605 | 611 | 270 | 0.50 | 0.90 |
| Pica PX714 [h] | Wood | Chemical | Pellets; odor removal | 1730 | 502 | 300 | 0.58 | 0.69 |

[a] N. Cao et al., *Energy & Fuels*, 15: 1263 (2001).
[b] Surface area determined by the Brunauer-Emmet-Teller method by measuring the adsorption of $N_2$ at −196° C. and $CO_2$ at 0° C. onto the activated charcoal. See S. Brunauer et al., *J. Am. Chem. Soc.*, 60: 309 (1938).
[c] ASTM D3860-98, "Standard Practice for Determination of Adsorptive Capacity of Activated Carbon by Aqueous Phase Isotherm Technique" using methylene blue.
[d] Calgon Carbon Corp., Pittsburgh, PA.
[e] Asbury Carbons, Inc., Asbury, NJ.
[f] Barneby & Sutcliffe Corporation, Columbus, OH.
[g] NORIT Americas, Atlanta, GA.
[h] PICA USA, Inc., Columbus, OH.

5.4 Hydrophobic Coating Materials

The dosage form can further comprise at least one hydrophobic coating material disposed on at least a portion of the surface of the adsorbent or adsorbent/adverse agent. Without being limited by theory, it is believed that the hydrophobic coating material seals the pores and channels of the adsorbent material, thereby inhibiting or preventing any aqueous fluid, e.g., a gastric fluid, from entering the pore or lattice structure of the adsorbent material. In one embodiment, the hydrophobic coating material covers at least a portion of the adsorbent/adverse agent.

In one embodiment, the at least one hydrophobic material is selected from the group consisting of acrylic and methacrylic acid polymers and copolymers, alkylcelluloses, natural and synthetic waxes, water insoluble waxes, fatty alcohols, fatty acids, hydrogenated fats, fatty acid esters, fatty acid glycerides, hydrocarbons, hydrophobic and hydrophilic polymers having hydrocarbon backbones, and mixtures of any two or more of the foregoing.

In one embodiment, the at least one hydrophobic coating material include, e.g., esters of glycerol; fatty acids such as stearic acid and isostearic acid; alcohols such as stearyl alcohol, isostearyl alcohol, cetyl alcohol and cetostearyl alcohol; beeswax; hydrogenated castor oil, and hydrogenated cottonseed oil; and mixture thereof. In another embodiment, the hydrophobic coating material is stearyl alcohol.

5.5 Hydrophobic Matrix Materials

In certain embodiments, the dosage form and pharmaceutical compositions of the invention can further comprise a hydrophobic matrix material. The hydrophobic matrix material can be the same or different from the hydrophobic coating material. The hydrophobic matrix material can control, at least in part, the release characteristics of the active agent and the adverse agent; and can further prevent, inhibit or delay the release of the adverse agent. Hydrophobic matrix materials useful in the present invention include those that are known in the art to be insoluble or to have a low solubility in the gastrointestinal tract. Such materials include, but are not limited to, a hydrophobic material selected from the group consisting of acrylic and methacrylic acid polymers and copolymers, and alkylcelluloses. The matrix can also include additional hydrophobic materials such as zein, shellac, hydrogenated castor oil, hydrogenated vegetable oil or mixtures thereof In one embodiment, the hydrophobic matrix material includes acrylic polymers. Examples of suitable acrylic polymers include, tout are not limited to acrylic acid and methacrylic acid copolymers, methyl methacrylate-: copolymers, ethoxyethyl methacrylates, cyanoethyl methacrylates, aminoalkyl methacrylate copolymer, poly(acrylic acid), poly(methacrylic acid), methacrylic acid alkylamide copolymers, poly(methyl methacrylate), polymethacrylate, poly(methyl methacrylate) copolymer, poly(methacrylic acid) (anhydride), methyl methacrylate, polyacrylamide, aminoalkyl methacrylate copolymer, poly(methacrylic acid anhydride)-, and glycidyl methacrylate copolymers. Additional examples of suitable acrylic polymers include, but are not limited to, acrylic resins including copolymers synthesized from acrylic and methacrylic acid esters (e.g., the copolymer of acrylic acid lower alkyl ester and methacrylic acid lower alkyl ester) containing about 0.02 to 0.03 moles of a tri (lower alkyl)ammonium group per mole of acrylic and methacrylic monomer.

The acrylic polymer can comprise one or more ammonio methacrylate copolymers. Ammonio methacrylate copolymers are well known in the art, and are fully polymerized copolymers of acrylic and methacrylic acid esters with a low content of quaternary ammonium groups. In order to obtain a desirable dissolution profile for a given therapeutic agent, it might be necessary to incorporate two or more ammonio methacrylate copolymers having differing physical properties. For example, it is known that by changing the molar ratio of the quaternary ammonium groups to neutral (meth) acrylic esters, the permeability properties of the resultant coating can be modified. One skilled in the art will readily be able to combine monomers to provide-a copolymer that releases the therapeutic agent at the desired release rate. Copolymers of acrylate and methacrylate having a quaternary ammonium group functionality are commercially available as EUDRAGIT RS and EUDRAGIT RL (Röhm Pharma, GmbH, Weiterstat, Germany). Preferred ammonio methacrylate resins include EUDRAGIT R-S in all forms, such as EUDRAGIT RS PO. EUDRAGIT RS is known to be a water-insoluble copolymer of ethyl acrylate (EA), methyl methacrylate (MM) and trimethylammonium ethyl methacrylate chloride (TAM) in which the molar ratio of EA:MM:T-AM is 1:2:0.01; see, e.g., U.S. Pat. No. 6,306,391. EUDRAGIT RS PO is known to be a powdered form of EUDRAGIT RS; see, e.g., U.S. Pat. No. 5,492,692 which is expressly incorporated herein by reference in its entirety for all purposes.

In one embodiment the hydrophobic matrix material includes a water insoluble cellulose polymer. In certain embodiments, the cellulose polymer is a cellulose ether, a cellulose ester, or a cellulose ester ether. Preferably, the cellulose polymers have a degree of substitution ("D.S.") on the anhydroglucose unit of from about zero up to and including about 3. As used herein the term D.S. means the average numbers of hydroxyl groups present on the anhydroglucose unit of the cellulose polymer that are replaced by a substituent group. Representative cellulose polymers include, but are not Limited to, polymers selected from cellulose acylate, cellulose diacylate, cellulose triacylate, cellulose acetate, cellulose diacetate, cellulose triacetate, mono-, di-, and tricellulose alkanylates, mono-, di-, and tricellulose arylates, and mono-, di-, and tricellulose alkenylates. Exemplary cellulose polymers include cellulose acetate having a D.S. of from about 1 to about 2 and cellulose acetate having a D.S. of from about 0.2 to about 3. Preferably, the cellulose polymer is ethylcellulose, cellulose acetate, cellulose propionate (low, medium, or high molecular weight), cellulose acetate propionate, cellulose acetate butyrate, cellulose acetate phthalate, or cellulose triacetate. A more preferred cellulose is ethylcellulose.

More specific cellulose polymers include cellulose propionate having a D.S. of about 1.8; cellulose acetate butyrate having a D.S. of about 1.8; cellulose triacylate having a D.S. of about 2.9 to 3, such as cellulose triacetate, cellulose trivalerate, cellulose trilaurate, cellulose tripalmitate, cellulose trisuccinate, and cellulose trioctanoate; cellulose diacylates having a D.S. of about 2.2 to 2.6 such as cellulose disuccinate, cellulose dipalmitate, cellulose dioctanoate, cellulose dipentanoate; and coesters of cellulose such as cellulose acetate butyrate, cellulose acetate octanoate butyrate, and cellulose acetate propionate.

In certain embodiments, the adsorbent/adverse agent can be intermixed with a hydrophobic matrix material. For example, a core comprising the adsorbent/adverse agent can further comprise up to about 50 wt. % of one or more hydrophobic matrix materials, preferably up to about 50 wt.

% of the one or more hydrophobic matrix materials, more preferably up to about 25 wt. % of the one or more hydrophobic matrix materials. The inclusion of a hydrophobic matrix material in the core can further reduce, delay or prevent the release or desorption of the adverse agent from the adsorbent material.

As noted above, the rate of release of the active agent and the adverse agent is controlled, in part, by the composition of the hydrophobic matrix material. One skilled in the pharmaceutical arts can affect these release rates by varying the composition hydrophobic matrix material, such variations being determined by routine experimentation in view of the present disclosure.

5.6 Active Agent

Any kind of active agent can be used in the dosage forms of the present invention. Examples of useful active agents include, but are not limited to, analgesics, anti-inflammatory agents, anthelmintic, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile-dysfunction-improvement agents, immunosuppressants, anti-protozoal agents, anti-thyroid agents, anxiolytic agents, sedatives, hypnotics, neuroleptics, β-blockers, cardiac ionotropic agents, corticosteroids, diuretics, anti-parkinsonian agents, gastrointestinal agents, histamine receptor antagonists, keratolytics, lipid regulating agents, anti-anginal agents, cox-2-inhibitors, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, and non-essential fatty acids. The dosage forms can comprise more than one active agent.

More specific examples of active agents include, but are not limited to, opioids, benzodiazepines, barbiturates, and stimulants, such as methylphenidate and amphetamines, dronabinol, glutethimide, methylphenidate, nabilone, anabolic steroids, methylprylon, ethchlorovynol, ethinamate, fenfluramine, meprobamate, pemoline, levomethadyl, benzphetamine, chlorphentermine, diethylpropion, phentermine, mebutamate, chlortermine, phenylacetone, dronabinol, nabilone, benphetamine, chloral hydrate, ethclorovynol, paraldehyde, midazolam, and detropropoxyphene.

In certain embodiments, the active agent is an opioid agonist. Useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, hydrocodone, hydromorphone, hydromorphodone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, pantopon, papavereturn, paregoric, pentazocine, phenadoxone, phendimetrazine, phendimetrazone, phenomorphan, phenazocine, phenoperidine, piminodine, piritramide, propheptazine, promedol, properidine, propoxyphene, propylhexedrine, sufentanil, tilidine, tramadol, pharmaceutically acceptable salts thereof, and mixtures of any two or more of the foregoing.

In certain embodiments, the opioid agonist is selected from the group consisting of hydrocodone, morphine, hydromorphone, oxycodone, codeine, levorphanol, meperidine, methadone, oxymorphone, buprenorphine, fentanyl and derivatives thereof, dipipanone, heroin, tramadol, etorphine, dihydroetorphine, butorphanol, levorphanol and mixtures thereof. In one embodiment, the opioid agonist is oxycodone, hydromorphone or hydrocodone.

The term "benzodiazepines" refers to benzodiazepine and drugs that are derivatives of benzodiazepine and are able to depress the central nervous system. Benzodiazepines include, but are not limited to, alprazolam, bromazepam, chlordiazepoxied, clorazepate, diazepam, estazolam, flurazepam, halazepam, ketazolam, lorazepam, nitrazepam, oxazepam, prazepam, quazepam, temazepam, triazolam, methylphenidate and mixtures of any two or more of the foregoing.

Barbiturates refer to sedative-hypnotic drugs derived from barbituric acid (2,4,6,-trioxohexahydropyrimidine). Barbiturates include, but are not limited to, amobarbital, aprobarbotal, butabarbital, butalbital, methohexital, mephobarbital, metharbital, pentobarbital, phenobarbital, secobarbital and mixtures of any two or more of the foregoing.

Stimulants refer to drugs that stimulate the central nervous system. Stimulants include, but are not limited to, amphetamines, such as amphetamine, dextroamphetamine resin complex, dextroamphetamine, methamphetamine, methylphenidate and mixtures of any two or more of the foregoing.

The active agent can be an agent intended for delivery to the colon, including, but not limited to, agents that act locally in the colonic region to treat a colon diseases such as irritable bowel syndrome, irritable bowel disease, Crohns disease, constipation, post operative atony, gastrointestinal infections, and therapeutic agents that deliver antigenic material to the lymphoid tissue. Active agents for the treatment of colon disease include, but are not limited to 5-ASA; steroids, such as hydrocortisone and budesonide; laxatives; stool softeners; octreotide; cisapride; anticholinergics; opioids; calcium channel blockers; DNA for delivery to the cells of the colon; glucosamine; thromboxane $A_2$ synthetase inhibitors, such as Ridogrel; 5HT3-antagonists, such as ondansetron; antibodies against infectious bacteria, such as *Clostridium difficile*; and antiviral agents, for example, for the prophylaxis of HIV.

Alternatively, the active agent can be an agent that is systemically active and for which absorption is improved in the colon region. Such drugs include polar compounds such as: heparins; insulin; calcitonins; human growth hormone (HGH); growth hormone releasing hormone (GHRH); interferons; somatostatin and analogues such as octreotide and vapreotide; erythropoietin (EPO); granulocyte colony stimulating factor (GCSF); parathyroid hormone (PTH); luteinising hormone releasing hormone (LHRH) and analogues thereof; atrial natriuretic factor (ANF); vasopressin; desmopressin; calcitonin gene related peptide (CGRP); and analgesics.

The active agent particles can further comprise hydrophobic materials, binders, plasticizers, excipients, and combinations of any two or more of the foregoing. Suitable matrix materials include those which allow release of the active agent at a rate sufficient to achieve the desired result, e.g., immediate release, sustained release or delayed release.

In one embodiment, a permeable matrix material is used, allowing for diffusive release of the active agent into the gastrointestinal fluid.

5.7 Adverse Agent

The adverse agent can be any pharmaceutical active agent which at least partially reduces or blocks the biological effect of an active agent or which creates an unpleasant effect when absorbed into an animal's or patient's blood stream. Examples of adverse agents include, but are not limited to, antagonists of any therapeutically active agonist. When an opioid agonist is used as the active agent in the dosage form of the present invention, an opioid antagonist can be used as the adverse agent. Likewise, when a benzodiazepine is used as the active agent in the dosage form of the present invention, a benzodiazepine antagonist can be used as the adverse agent. When a barbiturate is used as an active agent in the dosage form of the present invention, a barbiturate antagonist can be used as the adverse agent. When an amphetamine is used as an active agent in the dosage form of the present invention, an amphetamine antagonist can be used as the adverse agent. When the active agent is toxic when dosed above its normal therapeutic range, i.e., when there is a significant potential for an overdose, then an antidote of the toxic active agent can be used as the adverse agent.

In one embodiment, the adverse agent is an opioid antagonist. Opioid antagonists useful in the present invention include, but are not limited to, naloxone, naltrexone, nalmefene, nalbuphine, nalorphine, cyclazacine, cyclazocine, levallorphan, pharmaceutically acceptable salts thereof, and mixtures of any two or more of the foregoing.

Useful opioid antagonist salts include salts formed from an acid and the basic nitrogen group of an opioid antagonist. Examples of opioid antagonist salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and palmoate (i.e., 1, -methylene-bis-(2-hydroxy-3-naphthoate)) salts.

Other opioid antagonist salts include salts prepared from an antagonist having an acidic functional group, such as a carboxylic acid or sulfonic acid functional group, and a pharmaceutically acceptable inorganic or organic base. Suitable bases include, but are not limited to those identified above in Section 5.1 in the paragraph which references the term "pharmaceutically acceptable salt".

In certain embodiments, the opioid antagonist is nalmefene, naloxone, naltrexone, or a pharmaceutically acceptable salt thereof. In another embodiment, the opioid antagonist is a naltrexone salt, such as naltrexone hydrochloride.

Benzodiazepine antagonists that can be used as the adverse agent of the present invention include, but are not limited to, flumazenil.

Barbiturate antagonists which can be used as the adverse agent of the present invention include, but are not limited to, amphetamines, as described herein.

Stimulant antagonists that can be used as the adverse agent of the present invention include, but are not limited to, benzodiazepines, described herein.

In another embodiment of the present invention, the adverse agent is an agent that causes an undesired physiological reaction, such as emesis. This type of adverse agent can be used with any kind of therapeutic agent including an opioid, a benzodiazepine, a barbiturate, or a stimulant. Examples of emetic agents suitable for use as the adverse agent in the present invention includes any drag that safely and effectively induces vomiting after administration including, but not limited to, ipecac and apomorphine.

5.8 Methods for Preparing the Dosage Form of the Invention

5.8.1 The Adsorbent/Adverse Agent

In certain embodiments, the present invention relates to methods for preparing an adsorbent/adverse agent. For example, in some embodiments, the invention relates to methods for adsorbing the adverse agent from a liquid phase onto the adsorbent material. In one embodiment, the invention relates to a method for preparing an adsorbent/adverse agent comprising: providing an adsorbent material; contacting the adsorbent material with a liquid phase comprising the adverse agent for sufficient time to allow at least a portion of the adverse agent to adsorb onto the adsorbent; separating the adsorbent/adverse agent from the liquid phase; and, optionally, washing the adsorbent/adverse agent.

In one embodiment, the invention relates to methods for preparing a dosage form of the invention comprising extruding a composition comprising an adsorbent material and an adverse agent.

In another embodiment, the invention relates to methods for preparing a dosage form comprising: a) co-extruding i) a core comprising an adsorbent and an adverse agent; and (ii) a sheath which at least partially surrounds the core and preferably surrounds a majority of the core, to form an extrudate strand; and b) rendering the extrudate strand into a plurality of particles, e.g., by cutting.

In another embodiment, the invention relates to methods for preparing a dosage form comprising: a) co-extruding i) a core comprising an adsorbent and an adverse agent; ii) optionally, a sheath, which at least partially surrounds the core and preferably surrounds a majority of the core; and iii) a shell comprising an active agent, which at least partially surrounds the core and/or the optional sheath, to form an extrudate strand; and b) rendering the extrudate strand into a plurality of particles, e.g., by cutting.

In another embodiment, the invention relates to methods for preparing a dosage form comprising: a) forming a plurality of first particles comprising an active agent; b) co-extruding a plurality of second particles comprising i) a core comprising an adsorbent and an adverse agent; and ii) a sheath comprising a hydrophobic matrix material which at least partially surrounds the core, and preferably surrounds a majority of the core; and c) adding the first and second particles to a dosage form.

In another embodiment, the invention relates to methods for making a dosage form comprising: a) co-extruding i) a core sheet comprising an adsorbent and an adverse agent; ii) optionally, a sheath, which at least partially surrounds the core, preferably which surrounds a majority of the core, more preferably which substantially or completely surrounds the core; and iii) a shell including an active agent, which at least partially surrounds the sheath, preferably which surrounds a majority of the sheath, more preferably which substantially or completely surrounds the sheath, to form a multilayer extrudate sheet or laminate; and b) forming the multilayer extrudate sheet into dosage forms, such as tablets, caplets or a plurality of particles.

Adsorption (or sorption) processes and factors affecting the rate and extent of adsorption are well known in the art (see, e.g., *Perry's Chemical Engineer's Handbook*, 16:1-48 (6th ed. 1984); D. M. Ruthven, "Adsorption" *in Kirk-Othmer Encyc. of Chem. Technol.*, 4:493-528 (4th ed. 1995); and S. A. Gembicki et al, "Adsorption, Liquid Separation" in *Kirk-Othmer Encyc. of Chem. Technol.*, 4:573-600 (4th ed. 1995); the entire contents of each of which is expressly incorporated herein by reference in its entirety for all purposes).

In one embodiment, the absorbance step is performed in a reaction vessel comprising the adsorbent and liquid phase, optionally with mixing. In another embodiment, the adsorbent is contained in a column and the liquid phase is circulated through the adsorbent material. The rate and/or extent of adsorption can be monitored by, e.g., monitoring the change in concentration of the adverse agent in the liquid phase over time.

Suitable solvents for a process comprising adsorption from a liquid phase are those which can dissolve the adverse agent, but which will have a low tendency to redissolve the adverse agent once adsorbed onto the adsorbent material. Non-limiting examples of suitable solvents include water, aqueous solutions, such as Simulated Gastric Fluid (pH 1.2), Simulated Intestinal Fluid (pH 6.8), 0.1N hydrochloric acid solution and 0.1N phosphoric acid solution.

In one embodiment, an aqueous solvent is used in the solution adsorption process having a pH of from about 1 to about 7. More preferably, the pH of the aqueous solvent is from about 1 to about 4. Most preferably, the pH of the aqueous solvent can be about 1.

In certain embodiments, the temperature of the liquid phase used in the solution adsorption process can be varied to affect the rate and extent of adsorption. One skilled in the art can determine the optimal reaction temperature by routine experimentation.

The invention also relates to methods for preparing an adsorbent/adverse agent by a spraying a liquid phase comprising the adverse agent onto the adsorbent material. In one embodiment, the invention relates to a method for preparing an adsorbent/adverse agent comprising: providing an adsorbent material; providing a liquid phase comprising the adverse agent; adding the adsorbent material to a fluidized bed; fluidizing the adsorbent material; spraying the liquid phase onto the fluidized material; and, optionally, drying the adsorbent/adverse agent. In one embodiment, the method of drying the sprayed particles is selected from the group consisting of forced air, reduced pressure, heat and mixtures of any two or more of the foregoing.

The spray application process provides adsorbent that appears dry on the external surface, yet has internal surfaces that are "wet" with the liquid phase. Depending on the solvating power of the solvent, the adverse agent may or may not be adsorbed onto the surface of adsorbent material. However, removal of the solvent by, e.g., reduced pressure evaporation, optionally with heat, causes the adverse agent to be deposited on the surface of the adsorbent material as the liquid vehicle is evaporated. The spraying process allows the use of solvents that would otherwise desorb the adverse agent.

Non-limiting examples of solvents useful for the spray drying process include water as described above; alcohols including methanol, ethanol, n-propanol and i-propanol; dialkyl ethers including diethyl ether, di-propyl ether and d-butyl ether; and cyclic ethers such as tetrahydrofuran, and mixtures of any two or more of the foregoing.

In certain embodiments, the adsorbent/adverse agent further comprises a hydrophobic coating material. The coating material covers or seals the pores and channels of the adsorbent/adverse agent, thereby further delaying, reducing or eliminating release of the adverse agent. The hydrophobic coating material can be applied using any conventional coating means provided the method of application does not cause significant desorption of the adverse agent from the adsorbent/adverse agent.

In one embodiment, the method for applying the hydrophobic coating material comprises: providing a liquid phase comprising a hydrophobic matrix material; and spraying the adsorbent/adverse agent with the liquid phase.

In another embodiment, the method for applying the hydrophobic coating material comprises: providing a melt of the hydrophobic coating material; and applying the melt to the adsorbent/adverse agent. In one embodiment, the hydrophobic coating material is applied to the adsorbent/adverse agent by dip-coating the solid into the melt.

The invention also relates to methods for applying a hydrophobic coating material to the adsorbent/adverse agent during melt extrusion or granulation. In this embodiment, adsorbent/adverse agent and the hydrophobic coating material are added to a feed hopper together with other ingredients, and the mixture is extruded or compressed. Without being bound by theory, it is believed that energy required for the extrusion or compaction process is sufficient to cause the hydrophobic coating material to flow, and form a coating on the adsorbent/adverse agent.

Additional details regarding formulation and manufacture of dosage forms comprising an opioid agonist in releasable form and an opioid antagonist which is substantially not released are disclosed in U.S. Pat. No. 6,696,088 B2 to Oshlack et al., which is expressly incorporated herein by reference in its entirety for all purposes.

5.8.2 Methods for Extruding or Co-Extruding the Dosage Form

In certain embodiments, the present invention also relates to methods for preparing a pharmaceutical composition or dosage form comprising an adsorbent/adverse agent by extruding, such as by melt extruding, a core comprising an adsorbent/adverse agent. In one embodiment, the core further comprises a hydrophobic material.

In one embodiment, the invention relates to methods for preparing a plurality of adsorbent/adverse agent particles comprising: a) co-extruding a core comprising an adsorbent/adverse agent, and a sheath which at least partially surrounds the core and preferably surrounds a majority of the core, to form extrudate strands; and b) rendering the extrudate strands into a plurality of adsorbent/adverse agent particles, e.g., by cutting.

In one embodiment, the core comprises an adsorbent/adverse agent and a hydrophobic coating material, and the sheath comprises a hydrophobic matrix material.

In another embodiment, the invention relates to methods for preparing a dosage form comprising: a) forming a plurality of first particles comprising an active agent; b) co-extruding a plurality of second particles comprising an adsorbent/adverse agent, and, optionally, a sheath comprising a hydrophobic matrix material, which at least partially surrounds the core, and preferably surrounds a majority of the core; and c) combining the first and second particles together.

In another embodiment, the invention relates to methods for making a dosage form comprising: a) co-extruding a core comprising an adsorbent/adverse agent; a sheath, which at least partially surrounds the core, preferably which surrounds a majority of the core, more preferably which substantially or completely surrounds the core; and a shell including an active agent, which at least partially surrounds the sheath, preferably which surrounds a majority of the sheath, more preferably which substantially or completely surrounds the sheath, to form to form extrudate strands; and b) rendering the extrudate strands into a plurality of adsorbent/adverse agent particles, e.g., by cutting.

In another embodiment, the invention relates to methods for making a dosage form comprising: a) co-extruding a core comprising an adsorbent/adverse agent; optionally, a sheath, which at least partially surrounds the core, preferably which surrounds a majority of the core, more preferably which substantially or completely surrounds the core; and a shell including an active agent, which at least partially surrounds the sheath, preferably which surrounds a majority of the sheath, more preferably which substantially or completely surrounds the sheath, to form a multilayer extrudate sheet or laminate; and b) forming the multilayer extrudate sheet into dosage forms, such as tablets, caplets or a plurality of particles. In one embodiment, the method comprises the use of a rolling punch to render the multilayer extrudate sheet into particles.

In certain embodiments, the extrudates are used in dosage forms such as tablets, caplets or a plurality of particles.

Methods for preparing active agent-containing compositions or particles by extrusion and/or co-extrusion are well known. See, e.g., U.S. Pat. Nos. 5,958,452, 5,965,161 and 6,335,033, each of which is expressly incorporated herein by reference in its entirety for all purposes, which disclose known methods for extruding and forming pharmaceutical dosage forms, including dosage forms consisting of particles.

Co-extrusion methods to form two layer compositions or particles for administering an active agent are also known. See, e.g., U.S. Patent Application Publication No. 2002/0119197 A1, which is expressly incorporated herein by reference in its entirety for all purposes.

Methods for forming a dosage form of the invention by co-extrusion are discussed below. Unless otherwise stated, methods for preparing an extruded particle comprising only a core are similar to those for co-extrusion, except (1) only one hopper need be used to feed the core formulation and (2) the die need have only one orifice.

In one embodiment, a co-extrusion process is used to make pharmaceutical compositions or dosage forms comprising an adsorbent/adverse agent that releases the adverse agent in a limited amount in vivo following intact administration as intended to a patient. In one embodiment, the composition or dosage form comprises a co-extruded, adsorbent/adverse agent cylindrical particle having a core containing the adsorbent/adverse agent and which is at least partially radially surrounded along its length by a sheath that preferably does not contain any adverse agent. In a further embodiment, the co-extruded particles containing an adsorbent/adverse agent, such as an opioid antagonist, are placed in a gelatin capsule with particles containing an active agent.

The present invention further relates to methods for preparing a particulate adsorbent/adverse agent useful in a dosage form, comprising: charging a core formulation comprising an adsorbent/adverse agent and, optionally, a hydrophobic coating material into a first extruder; charging a shell formulation comprising an active agent into a second extruder; heating the formulations in the first and second extruders; co-extruding the formulations to form a strand comprising an adverse agent core radially surrounded by a shell comprising an active agent; and rendering the strand into particles, e.g., by cutting.

In another embodiment, the invention relates to methods for forming a multi-layer dosage form comprising: charging a core formulation comprising an adsorbent/adverse agent and, optionally, a hydrophobic coating material into a first extruder; charging a shell formulation comprising an active agent into a second extruder; heating the formulations in the first and second extruders; co-extruding the formulations to form a multilayer extrudate sheet or laminate; and forming the multilayer extrudate sheet into dosage forms, such as tablets, caplets or a plurality of particles. In one embodiment, the method comprises the use of a rolling punch to render the multilayer extrudate sheet into particles.

An example of an apparatus useful for the co-extrusion process of the present invention includes two powder-feeder hoppers, one for loading the adsorbent/adverse agent core components and one for loading the shell components. The adverse agent core components include the adsorbent/adverse agent; and, optionally, a hydrophobic coating material and additional materials including, but not limited to, additional retardants, binders, plasticizers and excipients, as described above. The shell components include the active agent, a controlled-release matrix material and additional materials including, but not limited to, additional retardants, binders, plasticizers and excipients as described below. The contents of each hopper are charged to an extruder. The outlet of each extruder is attached to the same coaxial die having multiple co-axial outlet orifices, thereby forming strands of extrudate with the adverse agent in the core of the strand and the shell radially surrounding the core.

Each extruder can, for example, be equipped with single or twin screws and heated barrels. Each screw extruder can, independently, be of the (i) counter-rotating (i.e., driven in opposite directions of rotation) non-intermeshing; (ii) co-rotating (i.e., driven in the same direction of rotation) non-intermeshing; (iii) counter-rotating intermeshing; or (iv) co-rotating intermeshing type. Each extruder can, independently, have a sole discharge port located at the end of its housing or a radial discharge port. Each screw extruder can, independently, have drive means at each end of the screw or a drive means present at only one end. Each screw extruder can, independently, have a length to diameter, or L/D, ratio of from 5-70, preferably from 20-60. Those in the art are familiar with such apparatuses, e.g., a Leistritz twin screw extruder having a vacuum attachment, a Leistritz Micro 18/GL 40D twin screw extruder, or a Warner & Pfleiderer model ZSK-30 twin screw extruder.

The temperature of each individually adjustable barrel zone of each extruder is set to the required temperature for a given formulation, and the extruder is allowed to thermally equilibrate, in one embodiment for about 30 minutes. The inside pressure of the twin screw extruder can be maintained from about 600 to about 980 mbar negative.

After a steady state temperature is attained, the contents of each powder-feeder hopper are fed into the separate pre-heated extruder, thereby forming in each extruder an intimately mixed molten mass, in one embodiment from about 30° C. to about 200° C. in temperature, preferably from about 50° C. to about 150° C., through heating and mixing, as it is driven through a series of zones by intermeshing screws and kneading elements. Optionally, a vent port can be present in the extruder. If it is desired to add a liquid component, independently of any powdered formulation, to a molten mass, the liquid can be injected into the extruder by any known means, for example, by an injection port supplied by a positive displacement pump, such as a gear pump.

The molten masses exiting each extruder are combined in a coaxial die, which is optionally downstream of a combining block and or a main gate adaptor, then passed through the exit orifice of the die. In one embodiment, the extrudate is formed as a single or multiple extruded strand(s) comprising an adverse agent core and a sheath which at least partially surrounds the core. In another embodiment, the extrudate is formed as a multi-layer sheet or laminate.

The rotation speed, in rpm, of each extruder is adjusted such that their combined output, at the die orifice, is from about 1 to about 20 kg/h or greater, preferably from about 6 to about 8 kg/h. The rotation speed of each extruder is one of the parameters that can be adjusted so that the output of each extruder yields the desired ratio of the core to the sheath.

The dimensions and/or cross-sectional profile of the die exit orifice can be adjusted to vary the thickness and shape of the resulting strand or sheet. For example, the orifice is not limited to a circular cross-sectional profile, but can be elliptical, square, rectangular, hexagonal, triangular, 5-pointed star-shaped, etc. In certain embodiments, an orifice having a circular cross-section can be adjusted to provide a strand having a diameter from about 0.1 mm to about 5.0 mm. The shape of the strand is determined by, among other factors, the shape of the die exit orifice opening and the method of rendering the strand into particles.

The strand produced from the co-extrusion process is thereafter conveyed away from the orifice and solidified by methods known to those in the art, for example, using a fan-cooled tunnel or a continuous movable belt upon which the strand(s) congeal and harden upon cooling. The strand is directed to a suitable device to render the extruded strand into particles by methods known to those in the art, for example, using laser cutting, a hot wire-cutter or a guillotine. Rendering the strand into particles can occur before, during or following congealing. In one embodiment, the hardened strand which results from the co-extrusion process is cut by a pelletizer, which can utilize rollers, a fixed knife, a rotating cutter and the like. The roller speed and cutter speed are set so as to produce particles of the desired size and release characteristics. Suitable instruments and systems are available from distributors such as Rand Castle Inc. of New Jersey. Other suitable apparatus will be apparent to those skilled in the art.

In one embodiment, the co-extruded strand is cut to form a number of cylinders as shown in FIG. 1, where the adverse agent-containing core is exposed at both ends of the cylinder. In any case, the compositions of the adverse agent-containing core and the sheath should be formulated accordingly to limit the rate of in vivo release of the adverse agent from the adsorbent adverse agent.

Where a sheet is produced from the co-extrusion process, the sheet is processed as described above for the strand, except the extrudate is formed as a multilayer sheet. The sheet can then be rendered into particles or tablets by any method, such as using a rolling punch. Methods for preparing compositions or particles by extrusion and/or co-extrusion are well known. See, e.g., U.S. Pat. Nos. 5,958,452, 5,965,161 and 6,335,033, each of which is expressly incorporated herein by reference in its entirety for all purposes, which disclose known methods for extruding and forming pharmaceutical dosage forms, including dosage forms consisting of particles.

In one embodiment, the co-extruded multilayer extrudate is rendered, e.g., by cutting, pinching, or crimping, to form a number of particulates, such as, for example, those shown in FIG. 1, where the adverse agent-containing core is substantially or completely enveloped by the sheath layer(s) and the shell layer(s). Advantageously, in a preferred embodiment, the action of a rolling punch device crimps or pinches the shell and sheath layers such that the sheath substantially or completely surrounds the core and the shell substantially or completely surrounds the sheath. In any case, the compositions of the core and the sheath should be formulated accordingly to limit or prevent the rate of in vivo release of the adverse agent from the adsorbent/adverse agent. Methods for forming extrudates into particles or tablets using devices such as a molding roll, a pinch device, a belt and a roller or tow rollers are disclosed in, for example, U.S. Pat. Nos. 6,120,802 and 5,073,379, each of which is expressly incorporated herein by reference in its entirety for all purposes.

In addition, it is to be understood that the particles can be any geometrical shape, such as a bead, a seed, a pellet, etc., depending upon the die exit orifice. In one embodiment, the particulates formed from strands will be spheroids with a diameter of from about 0.1 mm to about 3.0 mm. In another embodiment, the particulates formed from strands will be cylindrical with a length of from about 0.1 to about 3.0 mm and a diameter of from about 0.1 to about 3.0 mm.

When the particles are formed from a multilayer extrudate, the particles' shapes can further comprise modified cylindrical (e.g., having cylindrical sides with top and/or bottom curvature; having a substantially flat top and/or bottom with the sides having some degree of curvature, or a combination thereof), oval, elliptical, or the like, or some combination thereof, where "cylindrical" can include not only circular cross-sections but also one or more of the following cross-sections: triangular, square, rhomboidal, diamond, trapezoidal, pentagonal, hexagonal, octagonal, star-shaped (e.g., having 3, 4, 5, 6, or more points), or some combination thereof, including those shapes where the corners have been at least partially rounded. In one embodiment, the particulates formed can be ellipsoidal with dimensions (height, length, and width) from about 0.1 mm to about 3.0 mm. In another embodiment, the particulates formed can be cylindrical with similar dimensions.

Similarly, when the extrudate is a sheet, the dimensions and/or cross-sectional profile of the die orifice can be adjusted to vary the thickness and shape of the resulting multilayer sheet. For example, the die orifice is not limited to a rectangular cross-sectional profile, but can have a trapezoidal character (i.e., where the width of the top of the extrudate is smaller than width of the bottom of the extradate, or vice versa); can have some degree of curvature associated with the width and/or thickness of the multilayer sheet or laminate (i.e., top and/or bottom sides can have concave and/or convex curvature, such that the thickness changes across the width of the extrudate; in one embodiment, the die orifice opening has a very oblate oval shape); or can have any combination thereof. For example, an orifice having a circular cross-section can be adjusted to provide a multilayer sheet or laminate ha$^1$ving a diameter from about 0.1 mm to about 50 mm, alternately from about 0.5 mm to about 20 mm, for example from about 1 mm to about 10 mm.

Following their rendering into particles, the co-extruded particles are collected and can be used in any manner for which such solid pharmaceutical composition is used. Optionally, following their rendering into particles, the particles are passed through a separator using #16 TBC (approximately 0.054") and #26 TBC (approximately 0.031") opening screens and collected. In a preferred embodiment, co-extruded particles containing an adverse agent and particles containing an active agent are placed together in hard gelatin capsules for oral dosage to patients.

In one embodiment, the dosage form comprises a plurality of particles comprising a core, and, optionally, a shell which are placed in a gelatin capsule.

In one embodiment, the dosage form comprises a plurality of particles comprising a core, optionally, a sheath, and a shell which are placed in a gelatin capsule.

It will be apparent to one skilled in the art of pharmaceutical extrusion that the compositions and dimensions of the core, the optional sheath, and shell can be varied to achieve the desired release rate of the active agent. For example, by changing the co-extrusion die exit orifice dimensions, the thickness of the core, sheath and shell can be varied. In certain embodiments, the thickness of the core, the sheath and the shell can each be from about 0.05 mm to about 3.0 mm; in one embodiment, about 0.2 mm to about 1.0 mm. The desired thickness of the sheath can be determined, for example, by the dissolution rate of the hydrophobic matrix material and the thickness of the core. In certain embodiments, the thickness of the sheath is from about 0.05 mm to about 3.0 mm; in one embodiment, from about 0.1 mm to about 1.0 mm. The thickness of the shell can be adjusted based upon, for example, the shell composition and desired rate of release of the active agent. In certain embodiments, the thickness of the shell can be from about 0.05 mm to about 3.0 mm; in one embodiment, from about 0.1 mm to about 1.0 mm. In certain embodiments the thickness of the core, the optional sheath and the shell can be adjusted to provide a particle with a maximum dimension of about 5.0 mm or less; in one embodiment, about 3.0 mm or less.

In one embodiment, the dosage form comprises a plurality of MEM's. Optionally, following rendering and/or punching, the particles can be passed through a separator, for example, using #16 TBC and #26 TBC opening screens, and collected. In one embodiment, the particles are placed in hard or soft gelatin capsules for oral dosage to patients.

Figure 1B:
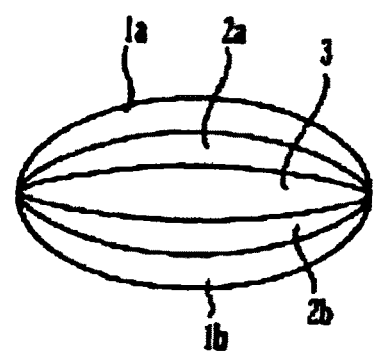
Figure 1C:
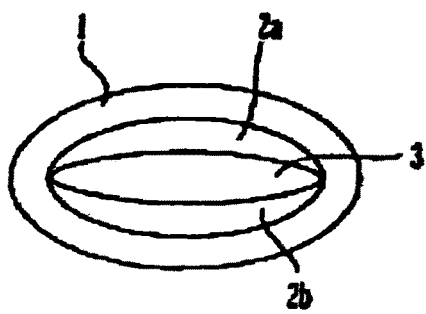

FIGS. 1a, 1b and 1c illustrate perspective views of three embodiments of a co-extruded particle or tablet of the present invention. En each of FIGS. 1a, 1b and 1c, core 3 comprises an adverse agent and a hydrophobic material. In FIG. 1a, sheath 2, which comprises a hydrophobic material, completely covers and surrounds core 3. Shell 1 comprises an active agent and a hydrophobic material, and completely covers and surrounds sheath 2.

In the embodiment shown in FIG. 1b, the sheath 2 comprises upper sheath component 2a and lower sheath component 2b. The sheath 2 surrounds the top and the bottom portions of core 3, but leaves a small amount of core 3 exposed along the side of the particle. Similarly, the shell 1 comprises uppers shell component 1a and lower shell component 1b. Shell 1 surrounds the top and the bottom of the sheath 2 while leaving a small portion of the sheath 2 and/or the core 3 exposed along the side of the particle.

In FIG. 1c, the sheath 2 comprises upper sheath component 2a and lower sheath component 2b which surround the top and the bottom of core 3 while leaving a small portion of core 3 exposed along the side. In this embodiment, the shell 1 completely covers and surrounds both sheath 2 and core 3.

In certain embodiments, the adsorbent/adverse agent is present in the core of an extruded particle or a co-extruded, multi-layer particle. The core containing the adsorbent/adverse agent can optionally comprise one or more binders, additional retardants, plasticizers, and/or excipients. Binders are useful for maintaining the integrity of the matrix and can also help to prevent, inhibit or delay the release of an adverse agent into the bodily fluid. Examples of binders include natural and synthetic waxes, water insoluble waxes, fatty alcohols such as stearyl alcohol, fatty acids such as stearic acid, hydrogenated fats, fatty acid esters, fatty acid glycerides, hydrocarbons, and hydrophobic and hydrophilic polymers having hydrocarbon backbones, water soluble polymers such as hydroxycelluloses, and mixtures of any two or more of the foregoing.

Plasticizers are useful when the hydrophobic matrix material contains a cellulose polymer or an acrylic polymer. Non-limiting examples of suitable plasticizers include, e.g., acetyl triethyl citrate and/or acetyl tributyl citrate.

The adsorbent/adverse agent-containing core can also include other excipients, which can be added to improve the processability of the formulation during extrusion and/or to improve the properties of the final product. Non-limiting examples of liquid excipients include water and oils, including those of petroleum, animal, vegetable, or synthetic origin, such as peanut oil, soybean oil, mineral oil, sesame oil, castor oil, triglycerides and the like. Examples of solid excipients include magnesium stearate, saline, gum acacia, gelatin, starch paste, talc, keratin, colloidal silica, urea and the like. Coloring agents can also be added to the core. The excipient can-be the same or different from the adsorbent materials.

In certain embodiments, the core of the dosage form of the present invention can comprise one or more of the materials disclosed in Section 5.8.2.1 with respect to the sheath.

5.8.2.1 Sheath

In certain embodiments, the dosage form of the present invention can include a sheath which at least partially surrounds the core containing the adsorbent/adverse agent, and preferably surrounds a majority of the core containing the adsorbent/adverse agent. In certain embodiments, the sheath preferably includes a hydrophobic matrix material and, optionally, binders, additional retardants, plasticizers and excipients. While, in certain embodiments, the sheath can contain a small percentage of adverse agent and/or active agent, it is preferred that the sheath does not contain any adverse agent or active agent.

In one embodiment, the hydrophobic matrix material of the sheath includes one or more materials selected from the group consisting of acrylic and methacrylic acid polymers and copolymers, and water insoluble alkylcelluloses as described above in relation to a hydrophobic coating material. The sheath can optionally comprise one or more additional hydrophobic materials, such as shellac, zein, hydrogenated castor oil, hydrogenated vegetable oil and mixtures thereof, as described above for the core.

The hydrophobic matrix material used in the sheath may or may not be the same as that optionally used as a hydrophobic coating material. Although the hydrophobic material used in the sheath will preferably be substantially insoluble in the gastrointestinal tract, this material could dissolve or biodegrade in vivo to some limited extent over time, thereby permitting the in vivo release from the core of a small amount of adverse agent from the adsorbent material. One skilled in the pharmaceutical arts can alter the rate of such release, for example, by altering the composition of the sheath, increasing the thickness of the sheath, surrounding a larger portion of the core with the sheath, varying the size and/or dimensions of the core and/or varying the composition of the sheath and/or core. These and other methods will be known to one skilled in the art or can be determined by routine experimentation in view of this disclosure.

In certain embodiments, the sheath can comprise from about 10% to about 99 wt. %, preferably from about 40 wt. % to about 95 wt. %, and more preferably from about 60 wt. % to about 90 wt. % of the one or more hydrophobic matrix materials.

The sheath can further comprise one or more additional retardants or one or more binders or plasticizers or excipients, or some combination thereof, such as those described in Section 5.8.2 for the adverse agent-containing core.

5.8.2.2 Shell

In certain embodiments, the dosage form of the present invention can include a shell comprising an active agent. The dosage form can provide any rate of release of the active agent in vivo from the shell following administration, such as immediate release, controlled release or delayed release. In certain embodiments, the dosage form provides a controlled release of the active agent, such as an opioid agonist. Formulations and methods of manufacture of controlled release dosage forms of opioid agonists are known in the art. For example, U.S. Pat. Nos. 5,958,452; 5,965,161; 5,968,551; 6,294,195 and 6,335,033, each of which is expressly incorporated herein by reference in its entirety for all purposes, disclose controlled release opioid agonist dosage forms. The disclosure of one or more of such patents includes details such as formulations, hydrophobic matrix materials, retardants, binders, plasticizers, and excipients, as well as extrusion methods for forming tablets, caplets and capsules containing MEMs, for controlled release opioid agonist dosage forms.

In certain embodiments, the active agent can be dispersed in a matrix which provides controlled release of the active agent in vivo following oral administration. Any suitable controlled-release matrix can be used to make the pharmaceutical compositions or dosage forms. Certain controlled-release matrices are known for oral formulations (see, e.g., Lee et al., "Controlled-Release Drug-Delivery Systems" in *Remington's: The Science and Practice of Pharmacy* 903-929 (20th ed. 2000), the disclosure of which is expressly incorporated herein by reference in its entirety for all purposes). In addition to the controlled release dosage forms disclosed in the above-identified patents and publications, other examples of useful controlled-release matrices are described in U.S. Pat. Nos. 6,143,328; 5,266,331; 5,549,912; 5,508,042; 5,656,295; 5,324,351; 5,356,467; and 5,472,712; each of which is expressly incorporated herein by reference in its entirety for all purposes.

The controlled-release matrix can include fusible hydrophobic material(s), optionally combined with hydrophilic material(s). The fusible hydrophobic material(s) can be, for example, a hydrophobic polymer or a natural or synthetic wax or oil, such as hydrogenated vegetable oil or hydrogenated castor oil, which can, for example, have a melting point of from about 45° C. to about 100° C., and in one embodiment from about 50° C. to about 90° C. The hydrophobic material can be the same as that used as the hydrophobic coating material. The hydrophilic material can be a hydrophilic polymer such as a hydroxycellulose; a water soluble fusible material such as polyethylene glycol; a water soluble particulate material such as lactose; or a slightly water soluble particulate material such as dicalcium phosphate.

While any known co-extrusion method can be used to make controlled release dosage forms according to the present invention, the preferred method is melt co-extrusion of the ingredients with suitable matrix materials. For example, the shell comprising an active agent dispersed in a controlled-release matrix can be prepared by, e.g., extruding the active agent with a suitable non-fusible material including, but not limited to, one or more of the following:

(a) Hydrophilic or hydrophobic polymers, such as gums, cellulose ethers, protein-derived materials, nylon, acrylic resins, polylactic acid, polyvinylchloride, starches, polyvinylpyrrolidones, and cellulose acetate phthalate. Of these polymers, cellulose ethers, for example, substituted cellulose ethers such as alkylcelluloses (e.g., ethylcellulose), $C_1$-$C_6$ hydroxyalkylcelluloses (e.g., hydroxypropylcellulose and hydroxyethyl cellulose), and acrylic resins (e.g., methacrylates such as methacrylic acid copolymers) can be used. The controlled-release matrix can conveniently contain from about 1 wt. % to about 80 wt. % of the hydrophobic and/or hydrophilic polymer.

(b) Digestible, long chain ($C_8$-$C_{50}$, in one embodiment $C_8$-$C_{40}$) substituted or unsubstituted hydrocarbons, such as fatty acids; hydrogenated vegetable oils; fatty alcohols, such as lauryl, myristyl, stearyl, cetyl or, in one embodiment cetostearyl alcohol; glyceryl esters of fatty acids, for example, glyceryl monostearate; mineral oils; and waxes, such as beeswax, glycowax, castor wax, and carnauba wax. Hydrocarbons having a melting point of from about 25° C. to about 90° C. are used in one embodiment. Of these long chain hydrocarbon materials, fatty (aliphatic) alcohols are useful in one embodiment. The controlled-release matrix can contain up to about 60 wt. % of at least one digestible, long chain hydrocarbon.

(c) Polyalkylene glycols. The controlled-release matrix can contain up to about 60 wt. % of at least one polyalkylene glycol. The polyalkylene glycol can be, for example, polypropylene glycol or, in one embodiment, polyethylene glycol. The number average molecular weight of the polyalkylene glycol is in one embodiment from about 200 to about 15,000 Daltons, and in another embodiment from about 400 to about 12,000 Daltons.

In one embodiment, a suitable controlled-release matrix for use in the dosage form of the invention can include one or more cellulose ethers or acrylic resins, or one or more $C_{12}$-$C_{36}$ aliphatic alcohols; in another embodiment, $C_{12}$-$C_{22}$, aliphatic alcohols and/or one or more hydrogenated vegetable oils. In one embodiment, a particularly suitable matrix includes one or more alkylcelluloses, or one or more $C_{12}$-$C_{36}$ aliphatic alcohols; in another embodiment, $C_{12}$-$C_{22}$, aliphatic alcohols and, optionally, one or more polyalkylene glycols. In another embodiment, the matrix contains from about 0.5 wt. % to about 60 wt. %, and in another embodiment, from about 1 wt. % to about 50 wt. %, of the cellulose ether.

The acrylic resin can be, for example, a methacrylate such as methacrylic acid copolymer USNF Type A (EUDRAGIT L), Type B (EUDRAGIT S), Type C (EUDRAGIT L 100-55), EUDRAGIT NE 30 D, EUDRAGIT E, EUDRAGIT RL, or EUDRAGIT RS (commercially available from Röhm Pharma GmbH, Weiterstat, Germany). In one embodiment, the matrix contains from about 0.5 wt. % to about 95 wt. % of acrylic resin, and in another embodiment from about 10 wt. % to about 50 wt. % of acrylic resin.

In the absence of polyalkylene glycol, the matrix in one embodiment contains from about 1 wt. % to about 40 wt. %, in another embodiment from about 2 wt. % to about 36 wt. % of the aliphatic alcohol. When polyalkylene glycol is present in the oral dosage form, then the combined weight of the aliphatic alcohol and the polyalkylene glycol in one embodiment constitutes from about 2 wt. % to about 40 wt. %, in another embodiment from about 2 wt. % to about 36 wt. % of the matrix.

The polyalkylene glycol can be, for example, polypropylene glycol or, in one embodiment, polyethylene glycol. The number average molecular weight of the polyalkylene glycol is in one embodiment from about 200 to about 15,000 Daltons, and in another embodiment from about 400 to about 12,000 Daltons.

5.8.3 Methods for Preparing Tablet Formulations

As noted above, the invention also relates to a tablet or particles comprising an adsorbent/adverse agent. Tablets comprising the adsorbent/adverse agent of the present invention can be prepared by conventional means (see, e.g., Rudnic et al., "Oral Dosage Forms" in *Remington's: The Science and Practice of Pharmacy* 858-885 (20th ed. 2000), which is expressly incorporated herein by reference in its entirety for all purposes). In one embodiment, the particles or tablets are prepared by granulating and compressing a formulation comprising an active agent and the adsorbent/adverse agent.

In another embodiment, the tablets are prepared by compressing a plurality of first particles comprising an active agent; and a plurality of second particles comprising an adsorbent/adverse agent.

In another embodiment, the particles or tablets are prepared by a granulating and compressing a dosage form comprising a core comprising an adsorbent/adverse agent and a shell comprising an active agent; wherein the shell at least partially covers the core.

It is to be understood that the particles or tablets can be any geometrical shape such as, for example, spherical, oval, pellet, etc., and can vary in size in any dimension depending on the method of manufacture, the amount and type of active agent and adsorbent/adverse agent, and the targeted patient. In certain embodiments, the tablet of the invention has a dimension in any direction from about 5 mm to about 75 mm; in another embodiment, the tablet has a dimension in any direction from about 5 mm to about 30 mm; and in another embodiment, the tablet has a dimension in any direction from about 5 mm to about 15 mm.

The particles or tablets of the invention can further comprise pharmaceutically acceptable hydrophobic coating materials as defined above in Section 5.8.2.1; excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); wetting agents (e.g., sodium lauryl sulphate); and other additives or excipients or as is well-known in the art. The tablets can be coated by methods well-known in the art provided such coating does not interfere with the intended use of the tablet. A non-limiting example of a coating process is spray coating. In one embodiment, the tablets are formed by dip coating.

Other methods for preparing tablets from melt-extruded compositions are described above.

5.9 Methods for Administration

The present invention is also directed to methods for treating a condition in a patient including administering a dosage form of the present invention to a patient in need of said treatment. The dosage form can be, for example, an oral dosage form, such as a tablet or capsule, or a rectal or vaginal dosage form, such as a suppository. In one embodiment, the condition is pain and the dosage form includes an opioid and an adsorbent/opioid antagonist. In certain embodiments, the dosage form is administered to a patient twice a day, and in other embodiments, once a day.

5.10 Amount Per Dosage Unit

In the dosage form of the present invention, the amount of the active agent per dosage unit is that which is an effective amount for its particular indication and is independent of the amount of the adverse-effect agent. For example, if the therapeutic agent is an opioid agonist, the amount of the opioid agonist in the dosage form of the present invention is from about 1 mg to about 800 mg, in one embodiment from about 5 mg to about 160 mg. One skilled in the art can readily determine, without undue experimentation, the amount of therapeutic agent needed for a particular indication.

The amount of the adverse agent in the dosage form of the present invention is such that the adverse agent can give the intended adverse effect if, when tampered with, a substantial amount of the adverse agent is released immediately from the dosage form and absorbed into an animal's blood. When, upon tampering with the dosage form, the adverse agent is intended to reduce or eliminate one or more of the pharmacological effects of the active agent, such as euphoria, the amount of the adverse agent in the dosage form is at least sufficient to reduce or eliminate those effects of the active agent when both agents are substantially or completely released from the dosage form and absorbed into an animal's blood after tampering has occurred.

For example, in one embodiment, when the adverse agent is an opioid antagonist, such as naltrexone or nalmefene, the amount of the opioid antagonist present in a dosage form of the present invention can be from about 0.1 mg to about 50 mg or more. The opioid antagonists cyclazocine and naltrexone, when administered orally, retain much of their efficacy with a long duration of action, approaching 24 h. Amounts of less than about 10 mg of these opioid antagonists are used in oral formulations of the invention.

When, upon tampering, the adverse agent is intended to cause an undesired physiological reaction, such as emesis, the amount of the adverse agent in the dosage form is at least sufficient to cause such effect upon release after tampering has occurred.

For safety reasons, the amount of the adverse agent present in the dosage form should not be harmful to humans even if it is all immediately released. One skilled in the art can readily determine, without undue experimentation, the amount of adverse agent needed to elicit the intended adverse effect without being harmful.

In certain embodiments of the present invention, the ratio of the therapeutic agent to the adverse agent in the dosage form can be from about 1:1 to about 50:1 by weight, in one embodiment from about 1:1 to about 20:1 by weight. In certain other embodiments, the ratio can be about 1:1 to about 10:1 by weight.

In non-limiting embodiments in which the opioid agonist is hydrocodone, the controlled release dosage forms can include analgesic doses from about 5 mg to about 80 mg of hydrocodone per dosage unit. In non-limiting embodiments where the opioid agonist is hydromorphone, it can be included in an amount from about 2 mg to about 64 mg hydromorphone hydrochloride per dosage unit. In non-limiting embodiments in which the opioid agonist is morphine, it can be present in the dosage form from about 2.5 mg to about 800 mg morphine per dosage unit. In non-limiting embodiments in which the opioid agonist is oxycodone, the dosage forms can include from about 2.5 mg to about 160 mg oxycodone, and in another embodiment from about 20 mg to about 30 mg oxycodone per dosage unit. Controlled-release oxycodone formulations are known in the art. In a non-limiting embodiment, the opioid agonist can be tramadol in an amount from about 25 mg to 800 mg tramadol per dosage unit. The dosage form can contain more than one opioid agonist, and the doses of each can be adjusted accordingly.

The term "unit dose" is defined for purposes of the present invention as the total amount of dosage form needed to administer a single desired dose of active agent (e.g., opioid agonist) to a patient.

5.11 Methods for Vaginal or Rectal Administration

As noted above, the present invention is also directed to administration of a dosage form comprising an active agent and an adsorbent/adverse agent, in the form of a suppository for absorption through the vagina or rectum. When administered as a suppository, the composition preferably includes a suppository base material. Any suppository base material can be used provided it does not dissolve the particulates. For example, cocoa butter is a traditional suppository base material, which can be modified by the addition of waxes to raise its melting point slightly. One or more water-miscible suppository base materials, such as polyethylene glycols of various molecular weights, can be included. When administered as a suppository, the combined concentration of the first and second plurality of particles in the suppository formulation is, in one embodiment, from about 5.0 wt. % to about 80 wt. % of the composition.

5.12 Kits

The present invention is also directed to a kit containing at least one dosage form of the invention. In one embodiment, the dosage form is present in a container, e.g., a bottle or box. In another embodiment, the kit further includes a set of instructions directing the use of the dosage form to treat a patient, e.g., for pain. In one embodiment, the instructions can be a printed label affixed to or printed on the container. In another embodiment, the instructions can include a printed sheet inserted into the container or into the packaging which contains the container. The instructions can also state that the dosage form and/or its usage are designed to reduce abuse, misuse or diversion of the dosage form.

All patents, applications, publications, test methods, literature, and other materials cited herein are hereby expressly incorporated by reference in their entirety for all purposes.

6. EXAMPLES

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the present invention.

6.1 Example 1

Preparation and Properties of Charcoal/Naltrexone

Example 1 describes a non-limiting method for making an adsorbent/adverse agent. The adsorbent used was DARCO activated charcoal obtained from EM Science, an affiliate of Merck KGaA of Darmstadt, Germany. The DARCO activated charcoal used was 20 to 40 mesh black granular charcoal which passed the USP absorptive power test (see *The United States Pharmacopeia*, 26:404 (2003)) for activated charcoal.

Adsorption of naltrexone: The activated charcoal (5.02 g) was added to a solution of naltrexone hydrochloride (504.26 mg) (obtained from Mallinkrodt, St. Louis, Mo.) in 0.1N HCl (900 mL). The resultant mixture was stirred at 100 rpm for 120 h at 37° C., and the adsorption (or uptake) of naltrexone hydrochloride into the activated charcoal was monitored by measuring the decrease in concentration of the naltrexone hydrochloride in the liquid phase using high performance liquid chromatography (HPLC). The data was used to calculate the amount of naltrexone adsorbed onto the activated charcoal, e.g., after 2 h, as follows:

$$\text{Adsorbed naltrexone} = (naltrexone_{(initial)}) \times \left(1 - \frac{HPLC \text{ peak } area_{(t=2h)}}{HPLC \text{ peak } area_{(t=0)}}\right)$$

$$\text{Adsorbed naltrexone} = (504.26 \text{ mg}) \times \left(1 - \frac{215860}{483568}\right) = 279.16 \text{ mg}$$

Figure 2:
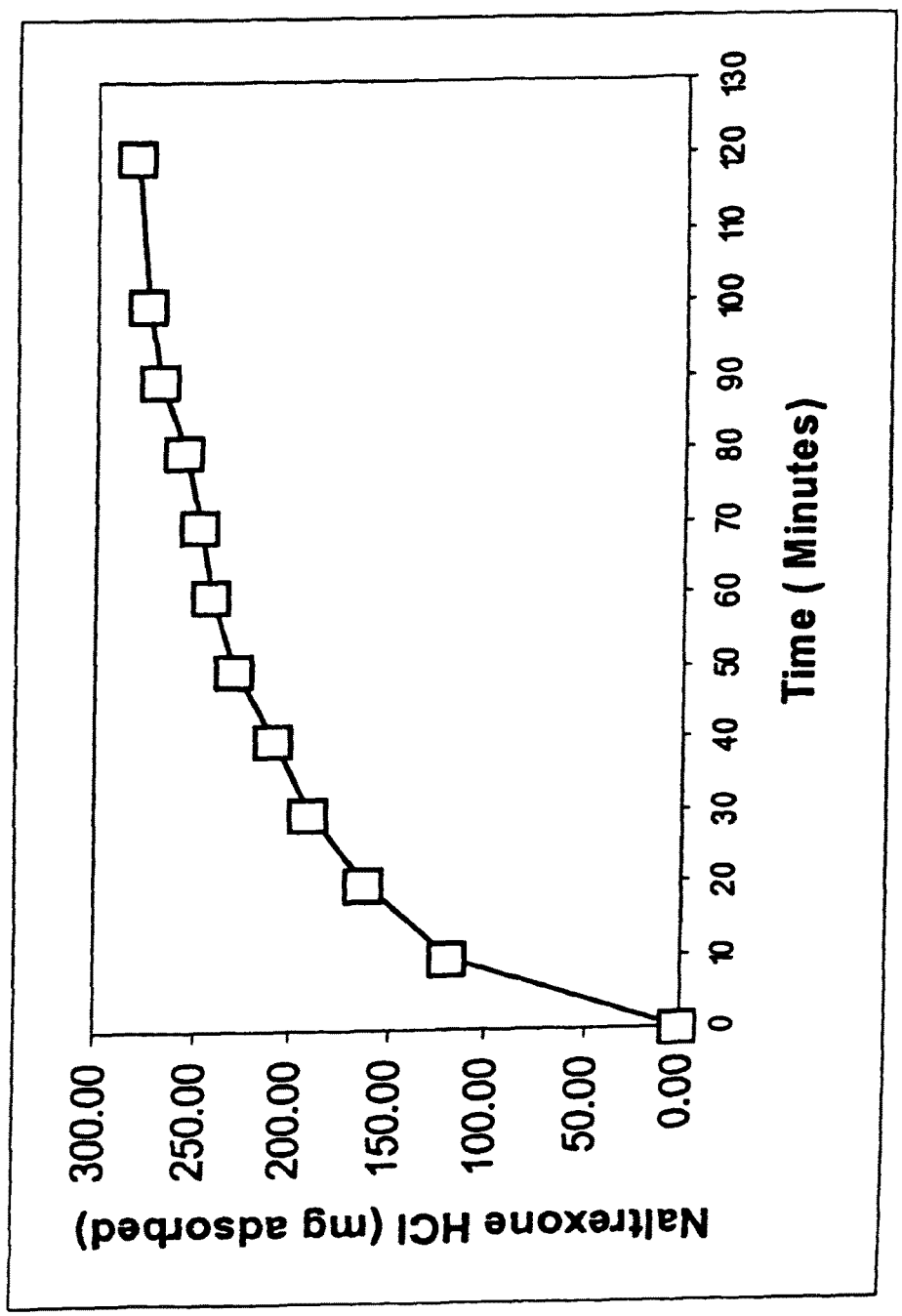
FIG. 2 is a graph illustrating adsorption of naltrexone hydrochloride (in mg) onto activated charcoal as a function of time.

The data are provided in Table 2 and plotted in FIG. 2.

TABLE 2

Adsorption of naltrexone hydrochloride onto activated charcoal from a 0.1N aqueous HCl solution at 37° C. as a function of time.

| Time, min | Naltrexone content in fluid, HPLC area % | Naltrexone content in fluid, mg | Naltrexone adsorbed onto the activated charcoal, mg | Naltrexone adsorbed from solution, % |
|---|---|---|---|---|
| 0  | 4.83568 | 504.26 | 0.00   | 0.00  |
| 10 | 3.70707 | 386.57 | 117.69 | 23.34 |
| 20 | 3.28801 | 342.87 | 161.39 | 32.01 |
| 30 | 3.01659 | 314.57 | 189.69 | 37.62 |
| 40 | 2.83574 | 295.71 | 208.55 | 41.36 |
| 50 | 2.64151 | 275.45 | 228.81 | 45.37 |
| 60 | 2.52683 | 263.50 | 240.76 | 47.75 |
| 70 | 2.46125 | 256.66 | 247.60 | 49.10 |

TABLE 2-continued

Adsorption of naltrexone hydrochloride onto activated charcoal from a 0.1N aqueous HCl solution at 37° C. as a function of time.

| Time, min | Naltrexone content in fluid, HPLC area % | Naltrexone content in fluid, mg | Naltrexone adsorbed onto the activated charcoal, mg | Naltrexone adsorbed from solution, % |
|---|---|---|---|---|
| 80 | 2.38100 | 248.29 | 255.97 | 50.76 |
| 90 | 2.27373 | 237.10 | 267.16 | 52.98 |
| 100 | 2.20620 | 230.06 | 274.20 | 54.38 |
| 120 | 2.15860 | 225.10 | 279.16 | 55.36 |

The results showed that substantially all of the naltrexone adsorption was completed within about 1.5 h. The mixture was vacuum filtered using a sintered glass frit. The resultant filter cake was maintained on the glass frit under dynamic vacuum to provide a charcoal adsorbent naltrexone adverse agent as a free-flowing powder ("Charcoal/Naltrexone"). Based on the data in FIG. 2, the calculated content of naltrexone hydrochloride in the Charcoal/Naltrexone at the end of the process (t=2 h) was 5.56 wt. %.

Figure 3:
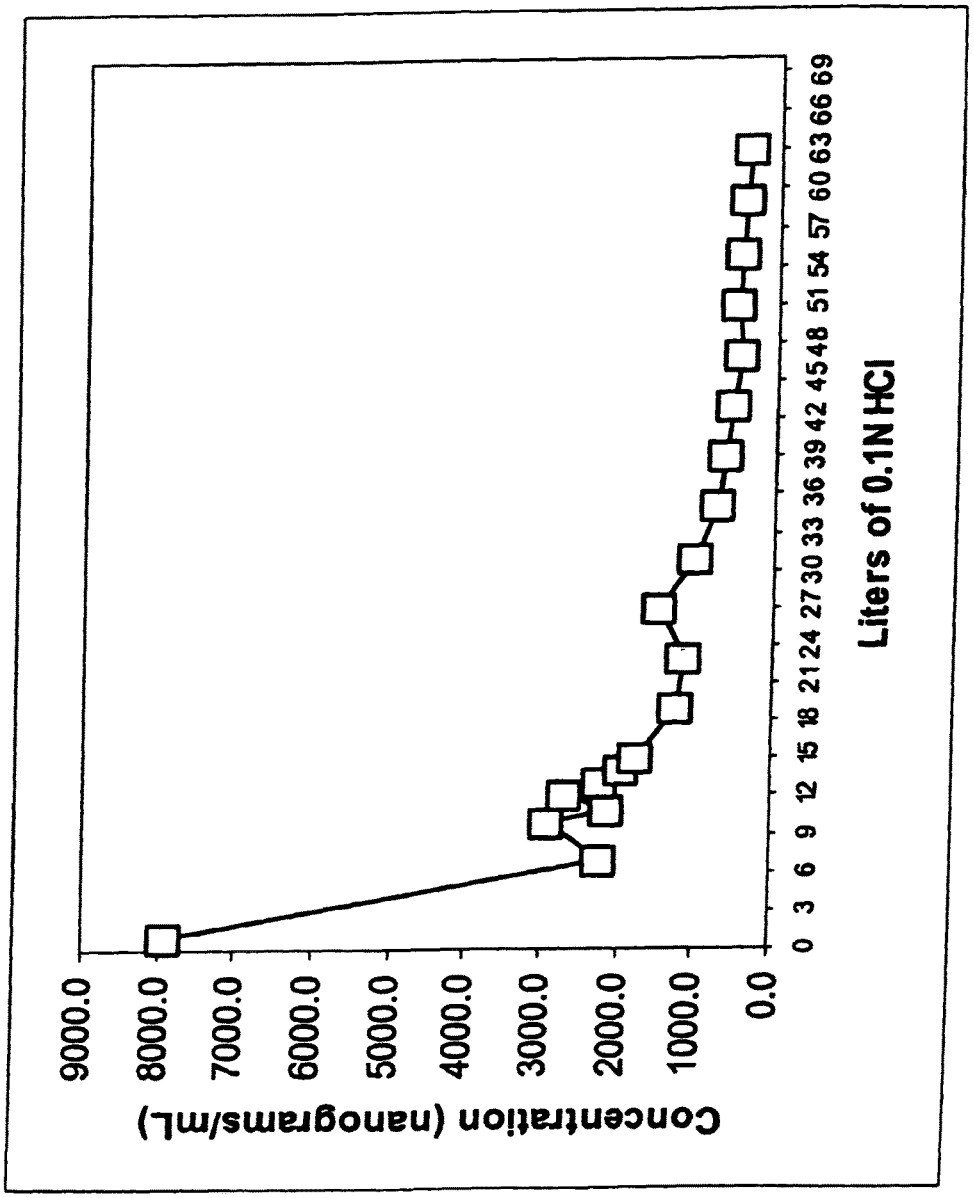
FIG. 3 is a graph illustrating the desorption of naltrexone hydrochloride (in ng mL of wash solution) from activated charcoal as a function of the liters of wash solution.

Dynamic Desorption of the Charcoal/Naltrexone:

The Charcoal/Naltrexone prepared as described above was transferred to a 1-liter sintered glass filter funnel, and washed at 25° C. with 63 1 L aliquots of 0. 1N HCl. The concentration of naltrexone hydrochloride in the wash filtrates was measured using HPLC as described above. The results are provided in Table 3 and plotted in FIG. 3.

TABLE 3

Desorption of naltrexone hydrochloride from Charcoal/Naltrexone as a function of volume of added 0.1N HCl at 25° C.

| Volume of 0.1N HCl added, liters | Naltrexone HCl extracted, ng/mL |
|---|---|
| 1 | 7899.8 |
| 7 | 2231.4 |
| 10 | 2904.3 |
| 11 | 2124.4 |
| 12 | 2690.3 |
| 13 | 2238.1 |
| 14 | 1921.7 |
| 15 | 1770.5 |
| 19 | 1246.0 |
| 23 | 1160.1 |
| 27 | 1497.6 |
| 31 | 996.9 |
| 35 | 742.6 |
| 39 | 651.7 |
| 43 | 566.1 |
| 47 | 467.2 |
| 51 | 492.4 |
| 55 | 442.6 |
| 59 | 426.8 |
| 63 | 383.4 |

The results showed that the majority of the desorption of naltrexone hydrochloride occurred during about the first 18 wash steps.

6.2 Example 2

Preparation and Properties of Acid-Washed Charcoal/Naltrexone

Acid washing: After the last wash, the resultant cake from Example 1 was dried on the filter flask to provide a dry free-flowing solid form of the acid-washed Charcoal/Naltrexone ("Acid-Washed Charcoal/Naltrexone"). The naltrexone hydrochloride content in the Acid-Washed Charcoal/Naltrexone was determined by grinding a portion of the solid to a fine powder using a mortar and pestle then extracting with methanol as follows. A weighed portion of the ground Acid-Washed Charcoal/Naltrexone (about 50 mg) was added to a 100 mL volumetric flask, 50 mL of methanol was added and, at about 25° C., the resultant mixture was sonicated for 15 minutes. After sonication, the mixture was allowed to cool to about 25° C. A 4.000 mL aliquot was removed via pipette, transferred to a 250 mL volumetric flask, and diluted to 250.00 mL with 0.1N HCl. The diluted mixture was shaken at 25° C. for 15-30 minutes, and the resultant cloudy liquid was filtered through Whatman HX nylon filter paper. The concentration of naltrexone in the filtrate was then determined using HPLC against a naltrexone standard. The mean naltrexone content (n=3 samples of ground Acid-Washed Charcoal/Naltrexone) was 3.06 wt. %.

Figure 4:
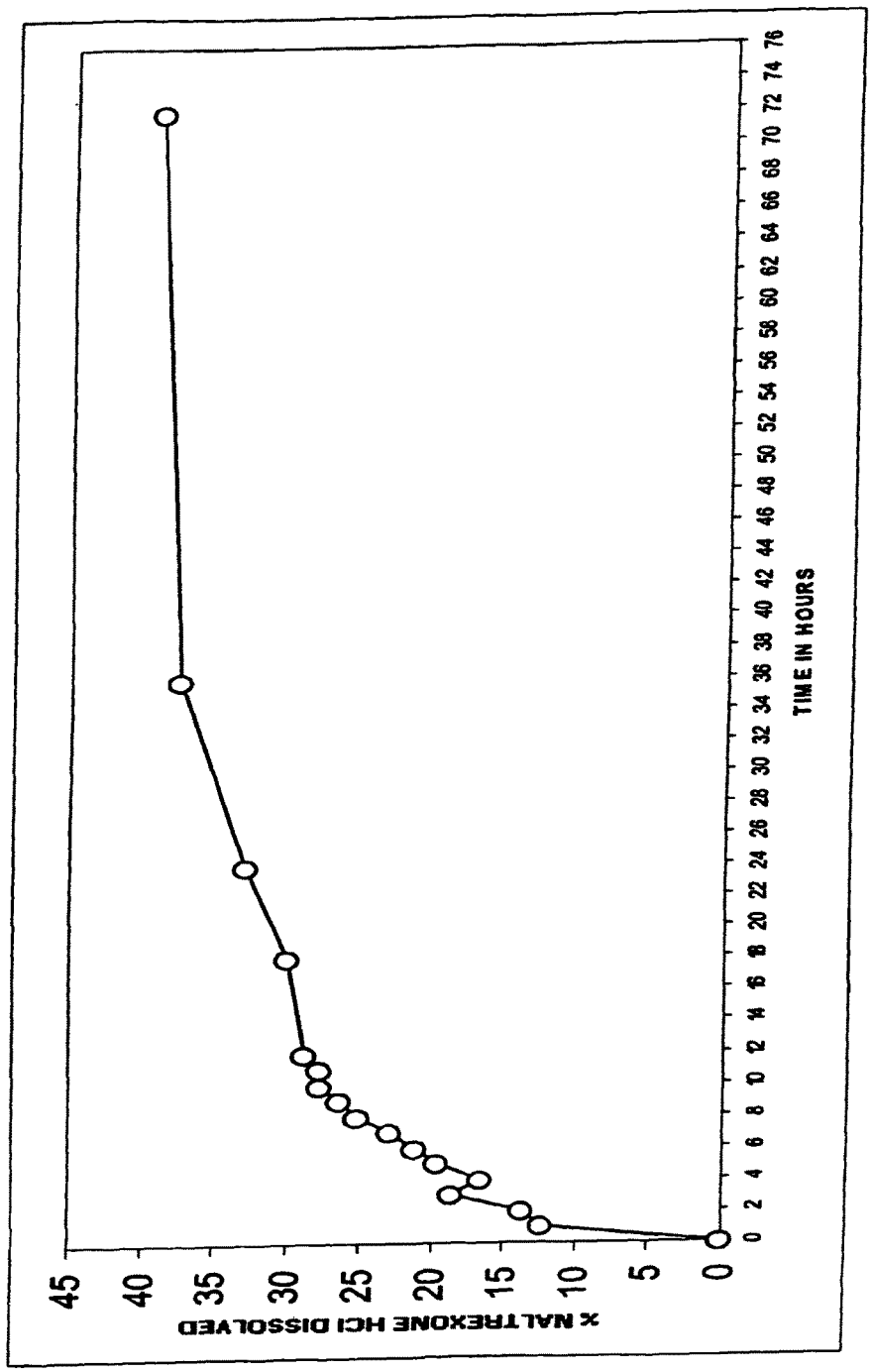
FIG. 4 is a graph illustrating the desorption of naltrexone hydrochloride from activate charcoal (in %) as a function of time during a simulated in vitro dissolution test.

Static desorption of the Acid-Washed Charcoal/Naltrexone: A portion of the Acid-Washed Charcoal/Naltrexone from above (about 50 mg) was added to a 2000 ml beaker equipped with a paddle containing 900 ml, of 0. 1N HCl at a temperature of 37° C. The contents of the beaker were mixed at 100 rpm for 72 h, and the naltrexone concentration in the liquid phase was monitored using HPLC. The data obtained in the static desorption study were normalized to the theoretical concentration of naltrexone if all the drag desorbed. The data are provided in Table 4 and plotted in FIG. 4, each point corresponding to the mean of n=6 samples of Acid-Washed Charcoal/Naltrexone.

TABLE 4

Desorption of naltrexone hydrochloride from Acid-Washed Charcoal/Naltrexone as a function of time during in a simulated in vitro dissolution test.

| Time, h | Naltrexone desorbed, mg | Naltrexone desorbed (dissolved), % | Naltrexone remaining adsorbed on the activated charcoal, mg | Naltrexone remaining adsorbed on the activated charcoal, wt. % |
|---|---|---|---|---|
| 0 | 0 | 0 | 1.53 | 3.06 |
| 1 | 0.19 | 12.4 | 1.34 | 2.68 |
| 2 | 0.21 | 13.7 | 1.32 | 2.64 |
| 3 | 0.29 | 18.7 | 1.24 | 2.49 |
| 4 | 0.25 | 16.6 | 1.28 | 2.55 |
| 5 | 0.30 | 19.7 | 1.23 | 2.46 |
| 6 | 0.33 | 21.3 | 1.20 | 2.41 |
| 7 | 0.35 | 23.0 | 1.18 | 2.36 |
| 8 | 0.38 | 25.1 | 1.15 | 2.29 |
| 9 | 0.40 | 26.3 | 1.13 | 2.26 |
| 10 | 0.43 | 27.8 | 1.10 | 2.21 |
| 11 | 0.43 | 27.8 | 1.10 | 2.21 |
| 12 | 0.44 | 28.7 | 1.09 | 2.18 |
| 18 | 0.46 | 30.0 | 1.07 | 2.14 |
| 24 | 0.50 | 32.8 | 1.03 | 2.06 |
| 36 | 0.57 | 37.4 | 0.96 | 1.92 |
| 72 | 0.60 | 39.0 | 0.93 | 1.87 |

The results showed that most, if not all, of the desorbable naltrexone desorbed within the first 36 h. Based on the content of naltrexone in the liquid phase after 72 h of static adsorption, the calculated content of naltrexone remaining in the Acid Washed Charcoal/Naltrexone was 61% of its initial value (3.06 wt. %) or about 1.9 wt. %.

The results of the above desorption studies showed that an adsorbent/adverse agent such as Charcoal/Naltrexone is useful for preventing undesirable release of the adverse agent.

6.3 Example 3

Preparation and Properties of Charcoal/Naltrexone Sealed with a Hydrophobic Matrix Material Sealing the Charcoal/Naltrexone with a Hydrophobic Material:

A beaker containing stearyl alcohol (about 10-15 g) was placed on a hot plate, heat was applied to melt the alcohol, and the melt was further heated to a temperature of 67° C. A portion of the Charcoal/Naltrexone prepared in Example 1 (200.41 mg) was added to a 100 mesh USP dissolution basket. The basket was fully immersed into the melt for 5-10 min and moved in an up and down reciprocating manner to aid in the coating of the Charcoal/Naltrexone. The basket was removed from the melt and allowed to cool to ambient temperature to provide the sealed Charcoal/Naltrexone ("Sealed Charcoal/Naltrexone") (472.45 mg) as a black solid with a white shade. The content of naltrexone hydrochloride in the Sealed Charcoal Naltrexone was calculated using the weight of Charcoal Naltrexone starting material and its naltrexone content (3.06 wt. %) together with the weight of the Sealed Charcoal/Naltrexone product.

$$\text{Naltrexone content} = (3.06 \text{ wt \%}) \times \frac{\text{(weight of Charcoal/Naltrexone)}}{\text{(weight of Sealed Charcoal/Naltrexone)}}$$

$$\text{Naltrexone content} = (3.06 \text{ wt \%}) \times \frac{(200.14 \text{ mg})}{(472.45 \text{ mg})} = 1.30 \text{ wt. \%}$$

Figure 5:
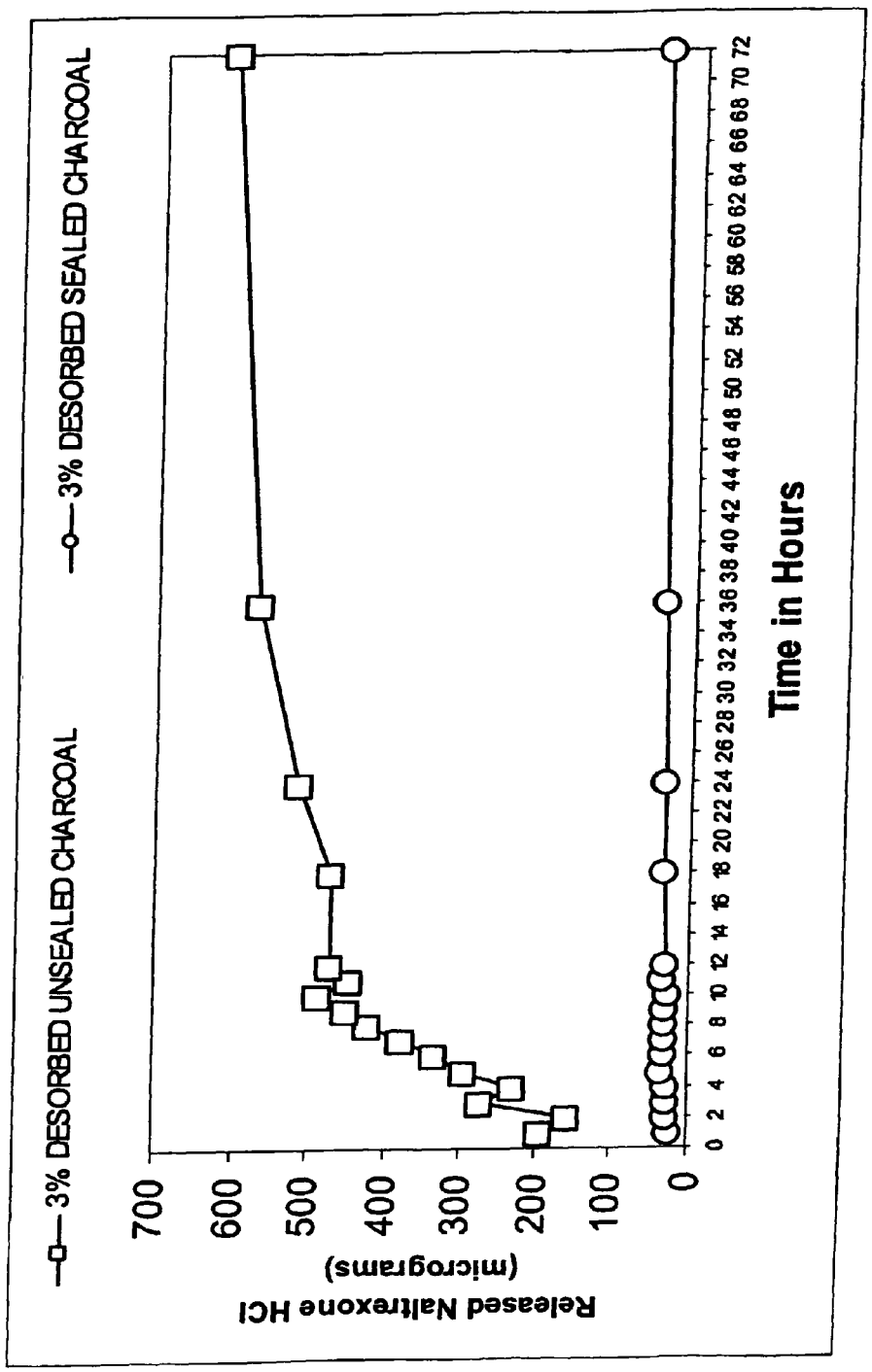
FIG. 5 is a comparative graph illustrating the desorption of naltrexone hydrochloride (in µg) as a function of time from a) sealed activated charcoal; and b) unsealed activated charcoal during a simulated in vitro dissolution test.

Static Desorption of the Sealed Charcoal/Naltrexone:

A portion of the Sealed Charcoal/Naltrexone (about 77 mg) was added to a 2000 mL beaker equipped with a paddle containing 0.1N HCl (900 mL), and the contents were mixed at 100 rpm for 72 h at 37° C. The naltrexone concentration in the liquid phase was monitored using HPLC. The data obtained in the static desorption study are provided in Table 5 and plotted in FIG. 5 (-o-o-o-), and represent the mean for n=6 samples of Sealed Charcoal/Naltrexone samples. For comparison, the same data were collected and plotted in FIG. 5 for the Charcoal/Naltrexone (- - - -) prepared in Example 1 (n=6 samples).

TABLE 5

Desorption of naltrexone hydrochloride as a function of time from unsealed activated charcoal (Charcoal/Naltrexone) and activated charcoal sealed with stearyl alcohol (Sealed Charcoal/Naltrexone) during simulated in vitro dissolution test.

| Time, h | Naltrexone desorbed from unsealed charcoal/ naltrexone, µg | Naltrexone desorbed from sealed charcoal/ naltrexone, µg |
|---|---|---|
| 1 | 192.054 | 23.494 |
| 2 | 157.087 | 24.027 |
| 3 | 272.241 | 26.714 |
| 4 | 227.314 | 26.799 |
| 5 | 294.844 | 31.508 |
| 6 | 333.870 | 28.384 |
| 7 | 375.422 | 37.240 |
| 8 | 420.648 | 28.247 |
| 9 | 449.391 | 27.687 |
| 10 | 484.948 | 26.549 |
| 11 | 444.769 | 31.781 |
| 12 | 471.184 | 27.838 |
| 18 | 471.023 | 31.393 |
| 24 | 516.712 | 33.809 |
| 36 | 569.693 | 35.227 |
| 72 | 609.872 | 42.137 |

After mixing Charcoal/Naltrexone for 72 h, the concentration of naltrexone hydrochloride in the liquid phase was about 610 ng/mL. In contrast, after mixing the Sealed Charcoal Naltrexone for 72 h, the concentration of naltrexone hydrochloride in the liquid phase was only about 42 ng/mL. The results showed that sealing Charcoal/Naltrexone with a suitable hydrophobic coating material farther prevented undesirable release of adverse agent from the adsorbent.

6.4 Example 4

Preparation of Acid-Washed Charcoal/Naltrexone Sealed with a Hydrophobic Matrix Material Sealing the Acid-Washed Charcoal/Naltrexone with a Hydrophobic Material:

The stearyl alcohol coating procedure described in Example 3 was repeated using the Acid-Washed Charcoal/Naltrexone prepared in Example 2. The content of naltrexone hydrochloride in the sealed Acid-Washed Charcoal Naltrexone ("Sealed Acid-Washed Charcoal/Naltrexone") was calculated from the weight of the Acid-Washed Charcoal Naltrexone starting material and it naltrexone content (3.06 wt. %) together with the weight of Sealed Acid-Washed Charcoal/Naltrexone. The mean naltrexone hydrochloride content in the Sealed Acid-Washed Charcoal/Naltrexone product (based on n=6 samples of Sealed Acid-Washed Charcoal/Naltrexone) was 1.30 wt. %.

In Vitro Desorption of the Sealed Acid-Washed Charcoal/Naltrexone:

A portion of the Sealed Acid-Washed Charcoal/Naltrexone (about 250 mg) was added to a USP type 2 dissolution vessel equipped with a paddle containing 900 mL of 0.1N HCl at 37° C., and the contents of the dissolution vessel were mixed at 100 rpm for 120 h. Analysis of the liquid phase (HPLC) showed that no detectable naltrexone was released over at least 120 h.

6.5 Example 5

Release of Naltrexone from Sealed Acid-Washed Charcoal Naltrexone Upon Tampering A sample of Sealed Acid-Washed Charcoal/Naltrexone from Example 4 was crushed using a mortar and pestle until a finely divided powder was formed. Weighed portions of the sample (about 0.025 g each) were added to scintillation vials containing 10.00 mL of either deionized distilled water (pH 6.5) or 40% ethanol in water. The resultant mixtures were extracted by shaking by hand for 10 minutes at 25° C. or 100° C. The content of naltrexone in the liquid phases of the samples was then determined using HPLC against a known naltrexone standard, and the results are shown in Table 6 below. Table 6 also includes comparative data for uncrushed Sealed Acid-Washed Charcoal/Naltrexone extracted at 25° C. in water or methanol.

TABLE 6

Results of naltrexone desorptive extraction from Sealed Acid-Washed Charcoal/Naltrexone in water and alcohols.

| Sample preparation/extraction solvent/temperature | Sealed Acid-Washed Charcoal/Naltrexone, mg | Naltrexone released, mg |
|---|---|---|
| Uncrushed/water/25° C. | 87.61 | ~0 |
| Uncrushed/methanol (neat)/25° C. | 85.20 | ~0 |
| Crushed/water/25° C. | 97.41 | 0.00076 |
| Crushed/40% ethanol/25° C. | 93.740 | 0.0092 |
| Crushed/40% ethanol/100° C. | 118.14 | 0.04123 |

The results of the study showed that Sealed Acid-Washed Charcoal/Naltrexone that is not subject to tampering, e.g., crushed, will not release a significant amount of naltrexone, i.e., about 0 mg of naltrexone were released. The results also showed that a sample of Sealed Acid-Washed Charcoal/Naltrexone that is subject to tampering, e.g., crashing followed by extraction with water or alcohol-containing solvent, will release naltrexone. The data in Table 6 further showed that the extent of release from a crashed sample of Sealed Acid-Washed Charcoal/Naltrexone increased at elevated temperature. The results indicate that Sealed Acid-Washed Charcoal/Naltrexone is useful in a tamper resistant dosage form.

What is claimed is:

1. A dosage form comprising an active agent, an adsorbent and an adverse agent, wherein the active agent is an opioid agonist and the adverse agent is an opioid antagonist, wherein the adsorbent comprises at least one material selected from the group consisting of an activated carbon and activated graphite, and wherein a majority of the adverse agent is adsorbed onto the adsorbent.

2. The dosage form of claim 1, wherein at least 80 wt. % of the adverse agent is adsorbed onto the adsorbent.

3. The dosage form of claim 2, wherein at least 90 wt. % of the adverse agent is adsorbed onto the adsorbent.

4. The dosage form of claim 1, wherein the adsorbent is activated charcoal.

5. The dosage form of claim 1, further comprising at least one hydrophobic material disposed at least on a portion of the outer surface of the adsorbent.

6. The oral dosage form of claim 5, wherein the at least one hydrophobic material is selected from the group consisting of acrylic and methacrylic acid polymers and copolymers, alkylcelluloses, natural and synthetic waxes, water insoluble waxes, fatty alcohols, fatty acids, hydrogenated fats, fatty acid esters, fatty acid glycerides, hydrocarbons, hydrophobic and hydrophilic polymers having hydrocarbon backbones, and mixtures of any two or more of the foregoing.

7. The dosage form of claim 6, wherein the at least one hydrophobic material is selected from the group consisting of glyceryl monosteareate; beeswax; cetyl alcohol; stearyl alcohol; hydrogenated castor oil; hydrogenated cottonseed oil; stearyl alcohol; stearic acid; and mixtures of any two or more of the foregoing.

8. The dosage form of claim 1, wherein the dosage form is an oral dosage form.

9. The dosage form of claim 1, wherein the dosage form releases about 0.5 mg or less of the adverse agent in vivo following intact administration.

10. The dosage form of claim 1, wherein the dosage form releases about 0.05 mg or less of the adverse agent in vivo following intact administration.

11. The dosage form of claim 1, wherein the active agent, adsorbent and adverse agent are in particulate form,
a plurality of first particles comprising the active agent; and
a plurality of second particles comprising the adsorbent and the adverse agent.

12. The dosage form of claim 11, wherein the adsorbent is activated charcoal.

13. The dosage form of claim 11, wherein the plurality of second particles, further comprise at least one hydrophobic material disposed on at least a portion of the outer surface of the adsorbent.

14. The dosage form of claim 13, wherein the at least one hydrophobic material is selected from the group consisting of acrylic and methacrylic acid polymers and copolymers, alkylcelluloses, natural and synthetic waxes, water insoluble waxes, fatty alcohols, fatty acids, hydrogenated fats, fatty acid esters, fatty acid glycerides, hydrocarbons, hydrophobic and hydrophilic polymers having hydrocarbon backbones, and mixtures of any two or more of the foregoing.

15. The dosage form of claim 14, wherein the at least one hydrophobic material is selected from the group consisting of glyceryl monosteareate; beeswax; cetyl alcohol; stearyl alcohol; hydrogenated castor oil; hydrogenated cottonseed oil; stearyl alcohol; stearic acid; and mixtures of any two or more of the foregoing.

16. The dosage form of claim 11, wherein the opioid agonist is selected from the group consisting of alfentanil, allylprodine, alphaprodine, anileridine, benzylmorphine, bezitramide, buprenorphine, butorphanol, clonitazene, codeine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacyl morphan, lofentanil, meperidine, meptazinol, metazocine, methadone, metophon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tramadol, tilidine, pharmaceutically acceptable salts thereof, and mixtures of any two or more of the foregoing.

17. The dosage form of claim 16, wherein the opioid agonist is selected from the group consisting of morphine, codeine, hydromorphone, hydrocodone, oxycodone, oxymorphone, dihydrocodeine, dihydromorphine, pharmaceutically acceptable salts thereof, and mixtures of any two or more of the foregoing.

18. The dosage form of claim 1, wherein the opioid agonist is selected from the group consisting of alfentanil, allylprodine, alphaprodine, anileridine, benzylmorphine, bezitramide, buprenorphine, butorphanol, clonitazene, codeine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacyl morphan, lofentanil, meperidine, meptazinol, metazocine, methadone, metophon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tramadol, tilidine, pharmaceutically acceptable salts thereof, and mixtures of any two or more of the foregoing.

19. The dosage form of claim 18, wherein the opioid agonist is selected from the group consisting of morphine, codeine, hydromorphone, hydrocodone, oxycodone, oxymorphone, dihydrocodeine, dihydromorphine, pharmaceutically acceptable salts thereof, and mixtures of any two or more of the foregoing.

20. The dosage form of claim 1, wherein the adsorbent comprises activated graphite.

* * * * *